United States Patent
Deisseroth et al.

(10) Patent No.: US 10,545,075 B2
(45) Date of Patent: Jan. 28, 2020

(54) METHODS AND COMPOSITIONS FOR PREPARING BIOLOGICAL SPECIMENS FOR MICROSCOPIC ANALYSIS

(71) Applicant: The Board of Trustees of the Leland Stanford Junior University, Palo Alto, CA (US)

(72) Inventors: Karl A. Deisseroth, Palo Alto, CA (US); Kwanghun Chung, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 77 days.

(21) Appl. No.: 14/403,050

(22) PCT Filed: Mar. 13, 2013

(86) PCT No.: PCT/US2013/031066
§ 371 (c)(1),
(2) Date: Nov. 21, 2014

(87) PCT Pub. No.: WO2014/025392
PCT Pub. Date: Feb. 13, 2014

(65) Prior Publication Data
US 2015/0144490 A1 May 28, 2015

Related U.S. Application Data

(60) Provisional application No. 61/681,551, filed on Aug. 9, 2012.

(51) Int. Cl.
| | | |
|---|---|---|
| G01N 1/40 | (2006.01) |
| G01N 27/447 | (2006.01) |
| G01N 1/30 | (2006.01) |
| G01N 1/31 | (2006.01) |
| G01N 33/483 | (2006.01) |

(52) U.S. Cl.
CPC ............ *G01N 1/31* (2013.01); *G01N 1/30* (2013.01); *G01N 1/40* (2013.01); *G01N 27/44743* (2013.01); *G01N 27/44747* (2013.01); *G01N 33/4833* (2013.01); *G01N 2001/4038* (2013.01)

(58) Field of Classification Search
None
See application file for complete search history.

(56) References Cited

U.S. PATENT DOCUMENTS

| | | |
|---|---|---|
| 3,129,158 A | 4/1964 | Raymond et al. |
| 3,208,929 A | 9/1965 | Raymond et al. |
| 3,346,479 A | 10/1967 | Natelson |
| 3,375,187 A | 3/1968 | Buchler |
| 3,563,880 A | 2/1971 | Anderson |
| 3,576,727 A | 4/1971 | Evatt |
| 3,616,454 A | 10/1971 | Levy et al. |
| 3,616,457 A | 10/1971 | Hjerten et al. |
| 3,674,678 A | 7/1972 | Post et al. |
| 3,865,712 A | 2/1975 | Davies |
| 3,989,613 A | 11/1976 | Gritzner |
| 4,088,561 A | 5/1978 | Anderson |
| 4,151,065 A | 4/1979 | Kaplan et al. |
| 4,292,161 A | 9/1981 | Hoefer et al. |
| 4,339,327 A | 7/1982 | Tyler |
| 4,375,401 A | 3/1983 | Catsimpoolas |
| 4,415,418 A | 11/1983 | Turre et al. |
| 4,479,861 A | 10/1984 | Hediger |
| 4,588,491 A | 5/1986 | Kreisher et al. |
| 4,685,025 A | 8/1987 | Carlomagno |
| 5,451,500 A | 9/1995 | Stapleton |
| 5,475,426 A | 12/1995 | Kodama |
| 6,219,575 B1 | 4/2001 | Nemati |
| 6,232,092 B1 | 5/2001 | Rogers |
| 6,472,216 B1 | 10/2002 | Chiang |
| 6,722,395 B2 | 4/2004 | Overbeck et al. |
| 7,660,620 B2 | 2/2010 | Zeijlemaker et al. |
| 8,105,778 B2 | 1/2012 | Dirks et al. |
| 8,124,751 B2 | 2/2012 | Pierce et al. |
| 8,852,614 B2 | 10/2014 | Frank et al. |
| 2004/0137613 A1 | 7/2004 | Vacanti et al. |
| 2004/0267362 A1 | 12/2004 | Hwang et al. |
| 2005/0047640 A1 | 3/2005 | Eisfeld et al. |
| 2005/0119736 A1 | 6/2005 | Zilla et al. |

(Continued)

FOREIGN PATENT DOCUMENTS

| | | |
|---|---|---|
| CN | 103513411 A | 1/2014 |
| EP | 1438976 | 7/2004 |

(Continued)

OTHER PUBLICATIONS

Erturk et al. ("Erturk", Nature Protocols, 2012, 7, 1983-1995).*
Zhu et al. ("Zhu", Expert Rev Devices, 2011, 8, 607-626).*
Oosthuysen et al. (2006) "Bioprosthetic tissue preservation by filling with a poly (acrylamide) hydrogel" Biomaterials 27(9)2123-2130.
Albrecht et al. (2005) "Photo- and Electropatterning of Hydrogel-Encapsulated Living Cell Arrays" *Lab Chip* 5:111-118.
Bevis and Glick (2002) "Rapidly maturing variants of the Discosoma red fluorescent protein (DsRed)" *Nature Biotechnology* 20:83-87.
Ertürk et al. (2012) "Three-Dimensional Imaging of the Unsectioned Adult Spinal Cord to Assess Axon Regeneratoin and Glial Reponses after Injury" *Nature Medicine* 18(1):166-171.

(Continued)

*Primary Examiner* — Mark Halvorson
*Assistant Examiner* — Kauser M Akhoon
(74) *Attorney, Agent, or Firm* — Edward J. Baba; Bozicevic, Field & Francis LLP

(57) ABSTRACT

Methods and compositions are provided for preparing a biological specimen for microscopic analysis. These methods find many uses, for example in medicine and research, e.g., to diagnose or monitor disease or graft transplantation, to study healthy or diseased tissue, to screen candidate agents for toxicity and efficacy in disease modification. Also provided are reagents, devices, kits and systems thereof that find use in practicing the subject methods.

33 Claims, 20 Drawing Sheets

(56) References Cited

U.S. PATENT DOCUMENTS

| | | | |
|---|---|---|---|
| 2005/0130317 | A1 | 6/2005 | Ventzki et al. |
| 2005/0181973 | A1 | 8/2005 | Genove et al. |
| 2005/0256588 | A1 | 11/2005 | Sawa et al. |
| 2007/0134798 | A1 | 6/2007 | McCormick et al. |
| 2008/0124374 | A1 | 5/2008 | Freyman |
| 2010/0055733 | A1 | 3/2010 | Lutolf et al. |
| 2012/0081518 | A1 | 4/2012 | Liu et al. |
| 2012/0112069 | A1 | 5/2012 | Piltch |
| 2012/0196320 | A1 | 8/2012 | Seibel et al. |
| 2013/0065030 | A1 | 3/2013 | Tallant et al. |
| 2013/0094755 | A1 | 4/2013 | Lippert et al. |
| 2014/0030192 | A1 | 1/2014 | Deisseroth et al. |
| 2014/0220574 | A1 | 8/2014 | Tuschl et al. |
| 2015/0087001 | A1 | 3/2015 | Gradinaru et al. |
| 2015/0153560 | A1 | 6/2015 | Lippert et al. |
| 2015/0267251 | A1 | 9/2015 | Cai et al. |
| 2016/0290899 | A1 | 10/2016 | Deisseroth et al. |
| 2017/0068086 | A1 | 3/2017 | Tomer et al. |
| 2017/0219465 | A1 | 8/2017 | Deisseroth et al. |

FOREIGN PATENT DOCUMENTS

| | | |
|---|---|---|
| JP | 2003502649 | 1/2003 |
| WO | WO 1999036559 | 7/1999 |
| WO | WO 2000017355 | 3/2000 |
| WO | 2000077293 | 12/2000 |
| WO | WO 2005062938 | 7/2005 |
| WO | WO 2007/030012 | 3/2007 |
| WO | WO 2009022133 | 2/2009 |
| WO | WO2010014244 | 2/2010 |
| WO | WO 2010030358 | 3/2010 |
| WO | WO 2011111876 | 9/2011 |
| WO | WO 2012103343 | 8/2012 |
| WO | WO 2013191274 | 12/2013 |
| WO | WO2014005866 | 1/2014 |
| WO | WO2014056992 | 4/2014 |
| WO | WO 2012147965 | 7/2014 |
| WO | WO 2012161143 | 7/2014 |
| WO | 2014/182528 | 11/2014 |
| WO | 2015/041755 | 3/2015 |
| WO | WO 2015028453 | 3/2015 |
| WO | WO 2016023009 | 2/2016 |
| WO | WO 2016073941 | 5/2016 |
| WO | WO 2016117614 | 7/2016 |
| WO | WO 2016147812 | 9/2016 |
| WO | WO 2015022883 | 3/2017 |
| WO | WO2017096248 | 6/2017 |

OTHER PUBLICATIONS

Hern and Hubbell (1998) "Incorporation of adhesion peptides into nonadhesive hydrogels useful for tissue resurfacing" *J. Biomed. Mater. Res.* 39(2):266-276.
Huh and Bae (1999) "Synthesis and characterization of poly(ethylene glycol)/poly(I-lactic acid) alternating multiblock copolymers" *Polymer* 40(22):6147-6155.
Lee et al. (2010) "Hydrophobic nanoparticles improve permeability of cell-encapsulating poly(ethylene glycol) hydrogels while maintaining patternability" *PNAS USA* 107(48):20709-20714.
Matz et al. (1999) "Fluorescent proteins from nonbioluminescent *Anthozoa* species" *Nature Biotechnology* 17: 969-973.
Nagai et al. (2002) "A variant of yellow fluorescent protein with fast and efficient maturation for cell-biological applications" *Nature Biotechnology* 20(1):87-90.
Nguyen and Daugherty (2005) "Evolutionary optimization of fluorescent proteins for intracellular FRET" *Nature Biotechnology* 23(3):355-360.
Rizzo (2004) "An improved cyan fluorescent protein variant useful for FRET" *Nature Biotechnology* 22(4):445-449.
Shaner et al. (2005) "A guide to choosing fluorescent proteins" *Nature Methods* 10 2(12):905-909.

Shkrob et al. (2005) "Far-red fluorescent proteins evolved from a blue chromoprotein from Actinia equine" *Biochem J.* 392(Pt 3):649-654.
Wang et al. (2004) "Evolution of new nonantibody proteins via iterative somatic hypermutation" *PNAS USA* 101(48):16745-16749.
West and Hubbell (1999) "Polymeric Biomaterials with Degradation Sites for Proteases Involved in Cell Migration" *Macromolecules* 32(1):241-244.
Wiedenmann et al. (2002) "A far-red fluorescent protein with fast maturation and reduced oligomerization tendency from *Entacmaea quadricolor* (Anthozoa, Actinaria)" *PNAS USA* 99(18):11646-11651.
Ackerly et al. (2000) "Glutamate slows axonal transport of neurofilaments in transfected neurons" *J Cell Biol* 150(1):165-176.
Bergen et al. (2008) "Nonviral Approaches for Neuronal Delivery of Nucleic Acids" *Pharm Res* 25(5):983-998.
Bouard et al. (2009) "Viral vectors: from virology to transgene expression" *British journal of pharmacology* 157(2):153-165.
Davidson and Breakefield (2003) "Viral vectors for gene delivery to the central nervous system" *Nat Rev Neurosci* 4(5):353-364.
Dodt et al. (2007) "Ultramicroscopy: three-dimensional visualization of neuronal networks in the whole mouse brain" *Nat Methods* 4(4):331-336.
Elsabahy et al. (2011) "Non-viral nucleic acid delivery: key challenges and future directions" *Curr Drug Deliv* 8(3):235-244.
Fahrbach et al. (2013) "Rapid 3D light-sheet microscopy with a tunable lens" *Optics Express* 21(18):21010-21026.
Fletcher et al. (2010) "Cell mechanics and cytoskeleton" *Nature* 463(7280):485-492.
Giacca (2010) "Gene therapy" Dordrecht ; New York: Springer pp. 1-303.
Gradinaru et al. (2009) "Optical Deconstruction of Parkinsonian Neural Circuitry" *Science* 324(5925):354-359.
Jäderstad et al. (2010) "Communication via gap junctions underlies early functional and beneficial interactions between grafted neural stem cells and the host" *Proc Natl Acad Sci USA* 107(11):5184-5189.
Ma et al. (2005) "Potential of Nanofiber Matrix as Tissue-Engineering Scaffolds" *Tissue Eng* 11(1-2):101-109.
McLean et al. (2014) "Widespread neuron-specific transgene expression in brain and spinal cord following synapsin promoter-driven AAV9 neonatal intracerebroventricular injection" *Neurosci Lett* 576:73-78.
Papadakis et al. (2004) "Promoters and control elements: designing expression cassettes for gene therapy" *Curr Gene Ther* 4(1):89-113.
Seddon et al. (2004) "Membrane proteins, lipids and detergents: not just a soap opera" *Biochimica et Biophysica Acta* 1666:105-117.
Tomer and Deisseroth (2014). "Advanced Clarity Methods for Rapid and High-Resolution Imaging of Intact Tissues." pp. 37-44.
Turano (2012) "Role of Chitin in Alzheimer's disease: a new cytotoxic pathway" Dissertation submitted to University of Verona 74 pages.
Wittmer et al. (2009) "Silk Nanofibers for Biomaterials" *Material Research Society Conference* Session WW7: Polymer Nanofibers for Medicine and Biology I.
Zaber (2013) "Three-Axis Stages with Built in Controllers" Zaber Technologies Inc., pp. 1-3.
Zeiss (2013) "Zeiss Lightsheet Z.1 Sample Preparation." pp. 1-33.
Zhang et al. (2006) "Viral vectors for gene delivery in tissue engineering" *Adv Drug Deliv Rev.* 58(4):515-534.
Zhang et al. (2010) "Optogenic interrogation of neural circuits: technology for probing mammalian brain structures" *Nat Protoc* 5(3):439-456.
Zheng et al. (2005) "Molecular cloning and functional characterization of mouse chitotriosidase" *Gene* 29:357(1):37-46.
Barth et al. (2004) "Alteration of neuronal firing properties after in vivo experience in a FosGFP transgenic mouse" I Neurosci. 24, 6466-6475.
Battich et al. (2013) "Image-based transcriptomics in thousands of single human cells at single-molecule resolution" Nat Meth 1-10.
Bloodgood et al (2013) "The activity-dependent transcription factor NPAS4 regulates domainspecific Inhibition" Nature 503, 121-125.

(56) References Cited

OTHER PUBLICATIONS

Choi et al. (2014) "Next-Generation in Situ Hybridization Chain Reaction: Higher Gain, Lower Cost Greater Durability" ACS Nano 8, 4284—4294.
Choi et al. (2010) "Programmable in situ amplification for multiplexed imaging ofmRNA Expression" Nat. Biotechnol. 28, 1208-1212.
Chung et al. (2013) "Structural and molecular interrogation of intact biological systems" Nature 497, 332-337.
Ciafre et al. (2005) "Extensive modulation of a set of microRNAs in primary glioblastoma" Biochem. Biophys. Res. Commw1. 334, 1351-1358.
Denk et al. (2004) "Serial block-face scanning electron microscopy to reconstruct three-dimensional tissue nanostructure" PLoS Biol2, e329.
Dodt et al. (2007 "Ultramicroscopy: three-dimensional visualization of neuronal networks in the whole mouse brain". Nat Meth 4, 331-336.
Egen et al. (2012) "Three-dimensional imaging of solvent-cleared organs using 3D1SCO" Nature Protocols 7, 1983-1995.
Esteller et al. (2011). Non-coding RI'I"As in human disease. Nat Rev Genet 12, 861-874.
Flood et al. (2013) "Zeiss Lightsheet Z.1" School of Biology & Environmental Science, 1-34.
Garner et al. (2012) "Generation of a synthetic memory trace" Science 335, 1513-1516.
Guenthner et al. (2013) "Permanent genetic access to transiently active neurons via TRAP: targeted recombination in active populations" Neuron 78, 773-784.
Guzowski et al. (1999) "Environment-specific expression of the immediate-early gene Arc in hippocampal neuronal ensembles" Nat Neurosci 2, 1120-1124.
Hama et al. (2011). Scale: a chemical approach for fluorescence imaging and reconstruction of transparent mouse brain. Nat Neurosci 14, 1481-1488.
Hama et al. (2015) "ScaleS: an optical clearing palette for biological imaging" Nat Neurosci 1-14.
Ke et al. (2013) "In situ sequencing for RNA analysis in preserved tissue and cells" Nat Meih 10, 857-860.
Kuwajima et al. (2013) "ClearT: a detergent- and solvent-free clearing method for neuronal and nonneuronal Tissue" Development 140, 1364-1368.
Landgraf et al. (2007) "A mammalian microRNA expression atlas based on small RNA library sequencing". Cell 129, 1401—1414.
Lee et al. (2014) "Highly Multiplexed Subcellular Rt\JA Sequencing in Situ" Science 343, 1360-1363.
Li et al. (2015) "Fast immune labeling by electrophoretically driven infiltration for intact tissue imaging" Sci Rep 5, 10640.
Lin et al. (2011) "Functional identification of an aggression locus in the mouse hypothalamus" Nature 470, 221-226.
Lyford et al. (1995) "Arc, a growth factor and activity-regulated gene, encodes a novel cytoskeleton-associated protein that is enriched in neuronal dendrites" Neuron 14, 433-445.
Masuda et al. (1999) "Analysis of chemical modification of RNA from formalin-fixed samples and optimization of molecular biology applications for such samples" Nucleic Acids Research 27, 4436—4443.
Mattson et al. (1993) "A practical approach to crosslinking" Mol. Biol. Rep. 17, 167-183.
Nedivi et al. (1993) "Numerous candidate plasticity-related genes revealed by differential eDNA cloning" Nature 363, 718-722.
Nedivi et al. (2009). The Function of Activity-Regulated Genes in the Nervous System. Physiological Review 89, 1079-1103.
Oh et al. (2014) "A mesoscale connectome of the mouse Brain" Nature 508, 207-214.

Pang et al. (2009) "Oncogenic role of microRNAs in brain tumors" Acta Neuropathol. 117, 599-611.
Pena et al. (2009) "miRNA in situ hybridization in formaldehyde and EDC-fixed tissues". Nat Meth 6, 139-141.
Ramirez et al. (2013) "Creating a false memory in the hippocampus" Science 34L 387-391.
Reijmers et al. (2007) "Localization of a stable neural correlate of associative memory" Science 317, 1230-1233.
Renier et al. (2014) "iDISCO: a simple, rapid method to immunolabel large tissue samples for volume Imaging". Celll59, 896-910.
Renwick et al. (2013) "Multicolor microRNA FISH effectively differentiates tumor types". J. Clin. Invest. 123, 2694-2702.
Resch-Genger et al. (2008) "Quantum dots versus organic dyes as fluorescent labels". Nat Meth 5, 763-775.
Richardson et al. (2015) Clarifying Tissue Clearing Cell 162, 246-257.
Shen et al. (2004) "X-ray photoelectron spectroscopy and infrared spectroscopy study of maleimide-activated supports for immobilization of oligodeoxyribonudeotides". Nucleic Acids Research 32, 5973-5980.
Sheng et al. (1990) "Membrane depolarization and calcium induce c-fos transcription via phosphorylation of transcription factor CREB". Neuron 4, 571-582.
Simard et al. (2001) "Urea substitutes toxic formamide as destabilizing agent in nucleic acid hybridizations with RNA probes" Electrophoresis 22, 2679-2683.
Smeyne et al. (1992) "Fos-lacZ transgenic mice: mapping sites of gene induction in the central nervous system" Neuron 8, 13-23.
Song et al. (2012) "Hybridization chain reaction-based aptameric system for the highly selective and sensitive detection of protein". Analyst 137, 1396-1396.
Srinivasan et al. (2002) "Effect of fixatives and tissue processing on the content and integrity of nucleic acids" The American Journal of Pathology 161,1961-1971.
Staudt et al. (2007) "2,2'-thiodiethanol: a new water soluble mounting medium for high resolution optical Rnicroscopy" Microsc. Res. Tech. 70, 1-9.
Susaki et al. (2014) "Whole-brain imaging with single-cell resolution using chemical cocktails a.nd computational analysis" Cell 157, 726-739.
Tainaka et al. (2014). "Whole-body imaging with single-cell resolution by tissue decolorization" Cell 159,911-924.
Tomer et al. (2014) "Advanced Clarity for rapid and high-resolution imaging of intact tissues" Nature Protocols 9, 1682-1697.
Tymianski et al. (1997) "A novel use for a carbodiimide compound for the fixation of fluorescent and non-t1uorescent calcium indicators in situ following physiological experiments" Cell Calcium 21, 175-183.
Wanner et al. (2015). "Challenges of microtome-based serial block-face scanning electron microscopy in neuroscience" J Microsc 259, 137-142.
Wemersson et al. (2007) "Probe selection for DNA microarrays using OligoWiz" Nature Protocols 2, 2677-2691.
Yang et al. (2014) "Single-cell phenotyping within transparent intact tissue through whole-body clearing" Cell 158, 945-958.
Zeisel et al. (2015) "Cell types in the mouse cortex and hippocampus revealed by single-cell RNA-seq" Science 347, 1138-1142.
Zheng et al. (2015) "Simplified Clarity for visualizing immunofluorescence labeling in the developing rat brain" Brain Struct Funct 1-9.
Zhou et al. (2009) "Evidence for selective microRNAs and their effectors as common long-term targets for the actions of mood stabilizers" Neuropsychopharmacology 34, 1395-1405.

* cited by examiner

Step #1: Hydrogel monomer infusion (Day 1 - Day 3)

Step #2: Hydrogel-tissue hybridization (Day 3)

Step #3: Electrophoretic tissue clearing (Day 5 - Day 8)

FIG. 9 a  Hydrogel-embedded/non-ETC
2 days in Focusclear b  Hydrogel-embedded/non-ETC
8 days in Focusclear c  Hydrogel-embedded/non-ETC
4 days in 85% glycerol d  Hydrogel-embedded/ETC-cleared
2 days in 85% glycerol

METHODS AND COMPOSITIONS FOR PREPARING BIOLOGICAL SPECIMENS FOR MICROSCOPIC ANALYSIS

CROSS-REFERENCE TO RELATED APPLICATIONS

This application is a national phase patent application of PCT/US2013/031066, filed on Mar. 13, 2013, which claims priority benefit to the filing date of U.S. Provisional Patent Application Ser. No. 61/681,551, filed on Aug. 9, 2012, the disclosure of which application is herein incorporated by reference in its entirety.

FIELD OF THE INVENTION

This invention pertains to preparing biological specimens for microscopic analysis.

BACKGROUND OF THE INVENTION

To study complex organs and tissues, such as brain and tumor, it is necessary to understand its integrated 3-D structure and fine molecular details throughout the whole tissue. Current methods, exemplified by array tomography or serial block-face scanning electron microscopy can provide sub-cellular fine details, but involve prohibitively inefficient and damaging mechanical sectioning and reconstruction. Optical sectioning techniques combined with tissue clearing methods have been developed, in which light-scattering is reduced to increase the depth at which tissue can be imaged. While these methods can bypass laborious mechanical sectioning and reconstruction processes, they are not compatible with immunostaining/molecular phenotyping. What is needed is a technology for the preparation of biological tissue for microscopic analysis that maintains the 3-D integrity of the tissue and of the sub-cellular structures therein, while also making biomolecules within the tissue e.g., proteins, lipids, steroids, nucleic acids, and small molecules, accessible for labeling with molecular probes at deeper regions in the tissue. The present invention addresses these and other issues.

SUMMARY OF THE INVENTION

Methods and compositions are provided for preparing a biological specimen for microscopic analysis. These methods find many uses, for example in medicine and research, e.g., to diagnose or monitor disease or graft transplantation, to study healthy or diseased tissue, and to screen candidate agents for toxicity and efficacy in disease modification. Also provided are reagents, devices, kits and systems thereof that find use in practicing the subject methods.

In some embodiments, the present disclosure provides methods of preparing a biological specimen for microscopic analysis, the methods including fixing the specimen with a plurality of hydrogel subunits, polymerizing the hydrogel subunits to form a hydrogel-embedded specimen, and clearing the hydrogel-embedded specimen. In some embodiments, clearing the hydrogel-embedded specimen involves substantially removing a plurality of cellular components from the specimen. In some embodiments, the cellular components include lipids.

In some embodiments, clearing the hydrogel-embedded specimen comprises electrophoresing the specimen. In some embodiments, the specimen is electrophoresed using a buffer solution that comprises an ionic surfactant. In some embodiments, the ionic surfactant is sodium dodecyl sulfate (SDS). In some embodiments, the specimen is electrophoresed using a voltage ranging from about 10 to about 60 volts. In some embodiments, the specimen is electrophoresed for a period of time ranging from about 15 minutes up to about 10 days. In some embodiments, the methods further involve incubating the cleared specimen in a mounting medium that has a refractive index that matches that of the cleared tissue. In some embodiments, the mounting medium increases the optical clarity of the specimen. In some embodiments, the mounting medium comprises glycerol.

In some embodiments, the microscopic analysis is optical microscopy, laser microscopy, electron microscopy, and scanning probe microscopy. In some embodiments, fixing the specimen involves contacting the specimen with a paraformaldehyde. In some embodiments, the hydrogel subunits include an acrylamide. In some embodiments, polymerizing the specimen comprises thermal crosslinking.

In some embodiments, the methods further involve contacting the specimen with a polypeptide, nucleic acid, or small molecule. In some embodiments, the contacting involves electrophoresis, hydrodynamic pressure, ultrasonic vibration, solute contrasts, microwave radiation, or vascular circulation. In some embodiments, the polypeptide, nucleic acid, or small molecule includes a component that can be rendered visible when the specimen is microscopically analyzed. In some embodiments, the tissue is central nervous system (CNS) tissue. In some embodiments, the CNS tissue is a whole brain.

In some embodiments, the present disclosure provides methods of imaging a biological specimen by microscopy, the methods including preparing a biological specimen as described above and imaging the biological specimen with a microscope. In some embodiments, the microscope is an optical microscope, laser microscope, electron microscope, or a scanning probe microscope. In some embodiments, cellular or subcellular aspects of the specimen are labeled with one or more small molecules, nucleic acids or proteins transported into the prepared tissue. In some embodiments, the methods further involve removing one or more small molecules, nucleic acids, or proteins that were previously transported into the prepared tissue.

In some embodiments, the present disclosure provides methods of mapping the connectivity of nervous system tissue, the methods including preparing a nervous system tissue specimen as described above and imaging one or more neurons in the specimen with a microscope. In some embodiments, the subject methods further include labeling the one or more neurons in the specimen with a component that can be rendered visible when the specimen is microscopically analyzed. In some embodiments, the neurons are labeled before fixing the tissue. In some embodiments, the neurons are labeled after polymerizing the hydrogel.

In some embodiments, the present disclosure provides kits for preparing a tissue for microscopic analysis, the kits including a fixative and a plurality of hydrogel subunits. In some embodiments, the kits further include an apparatus for electrophoresing a three-dimensional hydrogel-embedded specimen to substantially remove a plurality of cellular components from the specimen. In some embodiments, the cellular components include lipids.

In some embodiments, the present disclosure provides systems for preparing a biological specimen for imaging, the systems including an apparatus for electrophoresing a three-dimensional hydrogel-embedded specimen to substantially remove a plurality of cellular components from the specimen, a power supply and a temperature-controlled buffer circulator. In some embodiments, the cellular components include lipids.

In some embodiments, the present disclosure provides electrophoretic tissue clearing devices, the devices including an electrophoresis chamber for containing a three-dimensional hydrogel-embedded specimen, a plurality of electrodes, a power supply, and a temperature-controlled buffer circulator. In some embodiments, the subject devices further include a buffer filtering component. In some embodiments, the subject devices further include a plurality of fluid inlet and/or outlet ports. In some embodiments, the subject devices further include a component configured to support the hydrogel-embedded specimen. In some embodiments, the component is configured to support the hydrogel-embedded specimen in a position that is substantially inside an electric field generated between two or more of the electrodes. In some embodiments, one or more of the electrodes comprises an expansion component for increasing the size of an electric field generated by the electrodes. In some embodiments, the expansion component comprises one or more S-shaped bends. In certain embodiments, the length and the width of the one or more electrodes are approximately equal. In some embodiments, the subject devices further include a lid that forms a fluid-tight and/or air-tight seal with the electrophoresis chamber.

In some embodiments, the present disclosure provides methods of preserving a biological specimen, the methods involving fixing the specimen with a plurality of hydrogel subunits, polymerizing the hydrogel subunits to form a hydrogel-embedded specimen, and clearing the hydrogel-embedded specimen. In some embodiments, the subject methods further involve storing the cleared hydrogel-embedded specimen in a mounting medium. In some embodiments, the subject methods further involve analyzing the cleared hydrogel-embedded specimen for evaluation, diagnosis, or prognosis of a pathological state. In some embodiments, the specimen is a biopsy specimen or an autopsy specimen. In some embodiments, the pathological state is cancer, immune system dysfunction, neuropsychiatric disease, endocrine/reproductive disease, cardiovascular/pulmonary disease, musculoskeletal disease, or gastrointestinal disease.

In some embodiments, the specimen includes normal tissue, and the method further involves analyzing the specimen to evaluate cell, tissue, organ or system function and/or relationships between cells and tissues, including during development. In some embodiments, the subject methods further involve conducting a genetic, transcriptomic, genomic, proteomic, metabolomic and/or drug screening analysis on the specimen. In some embodiments, the subject methods further involve storing the specimen for future analysis, assessment, or functionalization.

In some embodiments, the present disclosure provides systems for infusing hydrogel monomers into biological tissue and subsequently triggering the monomers to form a polymer, gel, mesh, or network with desired stiffness, transparency, pore size, conductivity, or permeability properties, the system including a biological specimen and a plurality of hydrogel subunits. In some embodiments, the subject systems further include nanoscale hardware devices, proteins, oligonucleotides, and/or fluorescent staining reagents. In some embodiments, the components of the system are activated or functionalized by energy or external signals such as heat, light, chemical triggers, and/or accelerators.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 9 is a collection of images showing optical tissue clearing of intact adult mouse brain using FocusClear™ and glycerol.

DETAILED DESCRIPTION OF THE INVENTION

Figure 1:
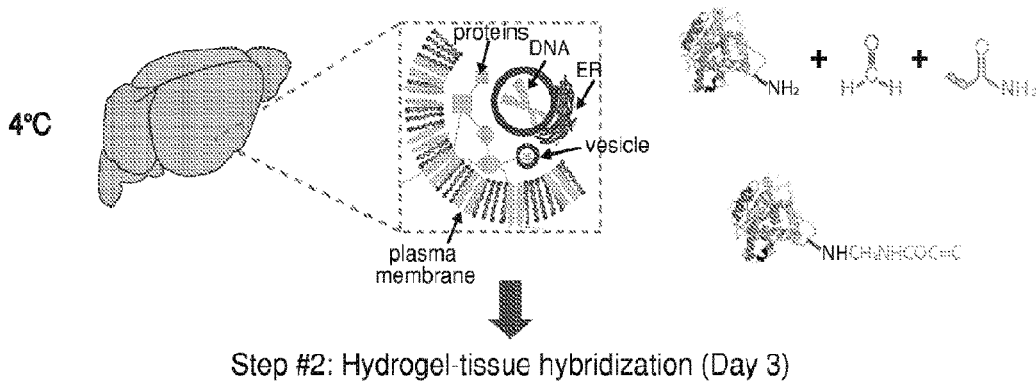
FIG. 1 is an illustration showing an overview of a process, termed "CLARITY," that facilitates imaging of tissues without tissue sectioning.
Figure 1:
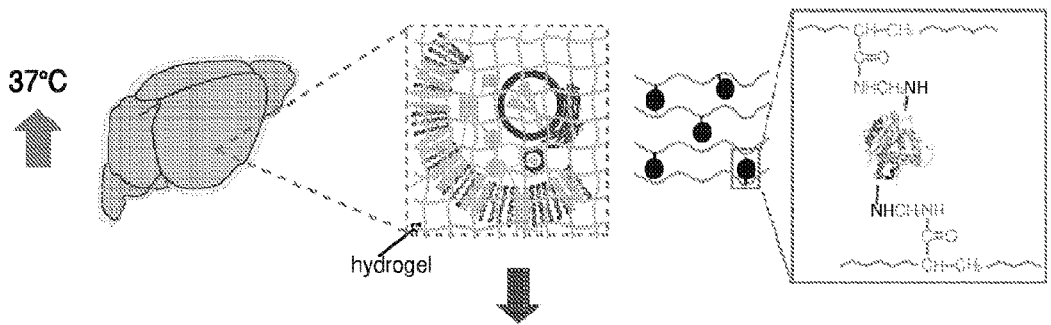
Figure 1:
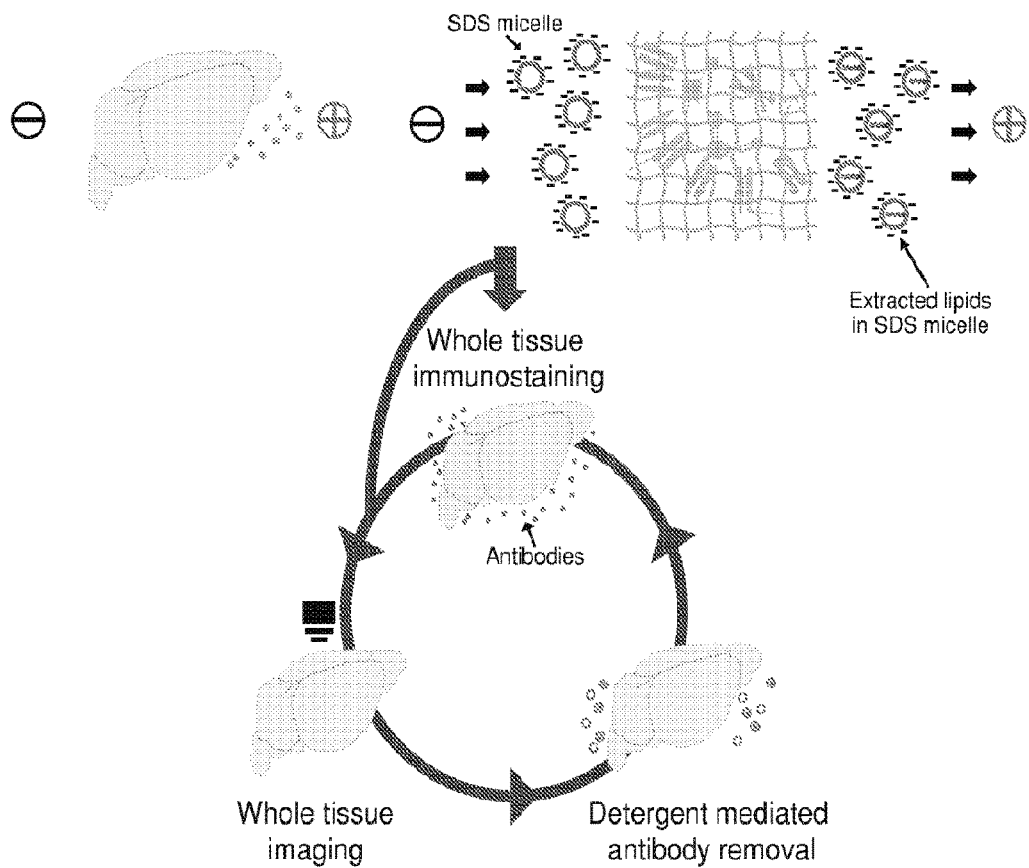

Methods and compositions are provided for preparing a biological specimen for microscopic analysis. These methods find many uses, for example in medicine and research, e.g., to diagnose or monitor disease or graft transplantation, to study healthy or diseased tissue, to screen candidate agents for toxicity and efficacy in disease modification. Also provided are reagents, devices, kits and systems thereof that find use in practicing the subject methods. These and other objects, advantages, and features of the invention will become apparent to those persons skilled in the art upon reading the details of the compositions and methods as more fully described below.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. Any steps of a method may be separated from another step of the method by an optional storage step, i.e. storage at room temperature, at 16° C., at 4° C., at −12° C., at −20° C., at −70° C., or on −130° C.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods

In aspects of the invention, methods are provided for preparing biological specimens for microscopic analysis. By "microscopic analysis" is meant the analysis of a specimen using techniques that provide for the visualization of aspects of a specimen that cannot be seen with the unaided eye, i.e., that are not within the resolution range of the normal eye. Such techniques may include, without limitation, optical microscopy (e.g., bright field, oblique illumination, dark field, phase contrast, differential interference contrast, interference reflection, epifluorescence, confocal, etc., microscopy), laser microscopy, electron microscopy, and scanning probe microscopy. By "preparing a biological specimen for microscopic analysis" is generally meant rendering the specimen suitable for microscopic analysis at an unlimited depth within the specimen.

In practicing the subject methods, a biological specimen is fixed in the presence of hydrogel subunits. By "fixing" the specimen it is meant exposing the specimen, i.e., cells of the specimen, to a fixation agent such that the cellular components become crosslinked to one another. By "hydrogel" or "hydrogel network" is meant a network of polymer chains that are water-insoluble, sometimes found as a colloidal gel in which water is the dispersion medium. In other words, hydrogels are a class of polymeric materials that can absorb large amounts of water without dissolving. Hydrogels can contain over 99% water and may comprise natural or synthetic polymers, or a combination thereof. Hydrogels also possess a degree of flexibility very similar to natural tissue, due to their significant water content. A detailed description of suitable hydrogels may be found in published U.S. patent application 20100055733, herein specifically incorporated by reference. By "hydrogel subunits" or "hydrogel precursors" is meant hydrophilic monomers, prepolymers, or polymers that can be crosslinked, or "polymerized", to form a three-dimensional (3D) hydrogel network. Without being bound by scientific theory, it is believed that this fixation of the biological specimen in the presence of hydrogel subunits crosslinks the components of the specimen to the hydrogel subunits, thereby securing molecular components in place, preserving the tissue architecture and cell morphology.

Any convenient fixation agent, or "fixative," may be used in the fixative/hydrogel composition to fix the specimen in the presence of hydrogel subunits, for example, formaldehyde, paraformaldehyde, glutaraldehyde, acetone, ethanol, methanol, etc. Typically, the fixative will be diluted in a buffer, e.g., saline, phosphate buffer (PB), phosphate buffered saline (PBS), citric acid buffer, potassium phosphate buffer, etc., usually at a concentration of about 1-10%, e.g. 1%, 2%, 3%, 4%, 5%, 6%, 7%, 8%, or 10%, for example, 4% paraformaldehyde/0.1M phosphate buffer; 2% paraformaldehyde/0.2% picric acid/0.1M phosphate buffer; 4% paraformaldehyde/0.2% periodate/1.2% lysine in 0.1M phosphate buffer; 4% paraformaldehyde/0.05% glutaraldehyde in phosphate buffer; etc. The type of fixative used and the duration of exposure to the fixative will depend on the sensitivity of the molecules of interest in the specimen to denaturation by the fixative, and will be known by the ordinarily skilled artisan or may be readily determined using conventional histochemical or immunohistochemical techniques, for example as described in Buchwalow and Böcker. *Immunohistochemistry: Basics and Methods*. Springer-Verlag Berlin Heidelberg 2010.

The fixative/hydrogel composition may comprise any convenient hydrogel subunits, such as, but not limited to, poly(ethylene glycol) and derivatives thereof (e.g. PEG-diacrylate (PEG-DA), PEG-RGD), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose and the like. In some instances, the hydrogel subunits may be modified to add specific properties to the hydrogel; for example, peptide sequences can be incorporated to induce degradation (see, e.g., West and Hubbell, 1999, Macromolecules, 32:241) or to modify cell adhesion (see, e.g. Hem and Hubbell, 1998, J. Biomed. Mater. Res., 39:266). Agents such as hydrophilic nanoparticles, e.g., poly-lactic acid (PLA), poly-glycolic acid (PLG), poly(lactic-co-glycolic acid) (PLGA), polystyrene, poly(dimethylsiloxane) (PDMS), etc. may be used to improve the permeability of the hydrogel while maintaining patternability (see, e.g., U.S. patent application Ser. No. 13/065,030; Lee W. et al. 2010 Proc. Natl. Acad. Sci. 107, 20709-20714). Materials such as block copolymers of PEG, degradable PEO, poly(lactic acid) (PLA), and other similar materials can be used to add specific properties to the hydrogels (see, e.g., Huh and Bae, 1999, Polymer, 40:6147). Crosslinkers (e.g. bis-acrylamide, diazirine, etc.) and initiators (e.g. azobisisobutyronitrile (AIBN), riboflavin, L-arginine, etc.) may be included to promote covalent bonding between interacting macromolecules in later polymerization steps.

Typically, the concentration and molecular weight of the hydrogel subunit(s) and modifying agents will depend on the selected polymer and the desired characteristics, e.g., pore size, swelling properties, conductivity, elasticity/stiffness (Young's modulus), biodegradability index, etc., of the hydrogel network into which they will be polymerized. For example, it may be desirable for the hydrogel to comprise pores of sufficient size to allow the passage of macromolecules, e.g., proteins, nucleic acids, or small molecules as described in greater detail below, into the specimen. The ordinarily skilled artisan will be aware that pore size generally decreases with increasing concentration of hydrogel subunits and generally increases with an increasing ratio of hydrogel subunits to crosslinker, and will prepare a fixative/hydrogel composition that comprises a concentration of hydrogel subunits that allows the passage of such macromolecules. As another example, it may be desirable for the hydrogel to have a particular stiffness, e.g., to provide stability in handling the embedded specimen, e.g., a Young's Modulus of about 2-70 $kN/m^2$, for example, about 2 $kN/m^2$, about 4 $kN/m^2$, about 7 $kN/m^2$, about 10 $kN/m^2$, about 15 $kN/m^2$, about 20 $kN/m^2$, about 40 $kN/m^2$, but typically not more than about 70 $kN/m^2$. The ordinarily skilled artisan will be aware that the elasticity of a hydrogel network may be influenced by a variety of factors, including the branching of the polymer, the concentration of hydrogel subunits, and the degree of cross-linking, and will prepare a fixative/hydrogel composition that comprises a concentration of hydrogel subunits to provide such desired elasticity. Thus, for example, the fixative/hydrogel composition may comprise an acrylamide monomer at a concentration of from about 1% w/v to about 20% w/v, e.g., about 2% to about 15%, about 3% to about 10%, about 4% to about 8%, and a concentration of bis-acrylamide crosslinker in the range of about 0.01% to about 0.075%, e.g., 0.01%, 0.02%, 0.025%, 0.03%, 0.04%, 0.05%, 0.06%, or 0.075%; or, for example, the fixative/hydrogel composition may comprise PEG prepolymers having a molecular weight ranging from at least about 2.5K to about 50K, e.g., 2.5K or more, 3.5K or more, 5K or more, 7.5K or more, 10K or more, 15K or more, 20K or more, but typically not more than about 50K, at a concentration in a range from about 1% w/w to about 50% w/w, e.g., 1% or more, 5% or more, 7.5% or more, 10% or more, 15% or more, 20% or more, 30% or more, 40% or more, and usually not more than about 50%. Concentrations of hydrogel subunits and modifiers that provide desired hydrogel characteristics may be readily determined by methods in the art or as described in the working examples below.

The fixative/hydrogel solution may be delivered to the specimen by any convenient method, e.g., perfusion, injection, instillation, absorption, application, immersion/submersion, etc. The specimen will typically be fixed in the presence of the hydrogel for 15 minutes or more, for example, for 30 minutes or more, 1 hour or more, 2 hours or more, 4 hours or more, 6 hours or more, 12 hours or more, in some instances, for 16 hours or more, 20 hours or more, or 24 hours or more.

Following fixation of the specimen, the hydrogel subunits are polymerized, i.e., covalently or physically crosslinked, to form a hydrogel network. Polymerization may be by any method including, but not limited to, thermal crosslinking, chemical crosslinking, physical crosslinking, ionic cross-linking, photo-crosslinking, irradiative crosslinking (e.g., x-ray, electron beam), and the like, and may be selected based on the type of hydrogel used and knowledge in the art. For example, mixing of an un-polymerized or partially polymerized resin with specific crosslinking chemicals results in a chemical reaction that forms cross-links. Crosslinking can be induced in materials that are normally thermoplastic through exposure to a radiation source, such as electron beam exposure, gamma-radiation, or UV light; for example, electron beam processing is used to polymerize the C type of crosslinked polyethylene. Other types of crosslinked polyethylene are made by addition of peroxide during extruding (type A) or by addition of a cross-linking agent (e.g. vinylsilane) and a catalyst during extruding and then performing a post-extrusion curing. Many polymers undergo oxidative cross-linking, typically when exposed to atmospheric oxygen. In some cases the reaction is more rapid than desired and thus polymerization reactions may involve the use of an antioxidant to slow the formation of oxidative cross-links. In other cases, e.g., when more rapid formation of cross-links by oxidation is desirable, an oxidizer such as hydrogen peroxide may be used to speed up the process. The length of time for polymerization will depend on the type of hydrogel subunits used and the chosen polymerization method, but will typically be about 15 minutes to about 48 hours, for example, 15 minutes or more, 1 hour or more, 2 hours or more, 3 hours or more, 4 hours or more, 6 hours or more, 12 hours or more, 16 hours or more, 24 hours or more, or in some instances, 48 hours. The optimal time and combination of reagents will be known to the ordinarily skilled artisan or may be determined empirically or from any number of publicly available resources (e.g., on the world wide web at piercenet.com; see also, Macroporous Polymers: Production Properties and Biotechnological/Biomedical Applications. Edited by Bo Mattiasson, Ashok Kumar, and Igor Yu. Galeaev. CRC Press 2010; and Crosslinking Reagents Technical Handbook, Pierce Biotechnology, Inc., 2006).

Once polymerized, the hydrogel-embedded (i.e., hydrogel-hybridized) specimen may be cleared. By "clearing" a specimen it is meant that the specimen is made substantially permeable to light, i.e., transparent. In other words, about 70% or more of the visual (i.e., white) light, ultraviolet light or infrared light that is used to illuminate the specimen will to pass through the specimen and illuminate only selected cellular components therein, e.g., 75% or more of the light, 80% or more of the light, 85% or more of the light, in some instances, 90% or more of the light, 95% or more of the light, 98% or more of the light, e.g. 100% of the light will pass through the specimen. This change in the optical properties of the specimen provides for the visualization of cellular and subcellular structures internal to the tissue.

Any treatment that forces cellular components, e.g., lipids, from the specimen, that draws cellular components, e.g., lipids, from a specimen, or that causes cellular components, e.g., lipids, to break down, i.e., dissolve, within a specimen may be used to clear the specimen, including, without limitation, exposure to organic solvents such as xylenes, ethanol or methanol, exposure to detergents such as saponin, Triton X-100 and Tween-20, exposure to ionic surfactants, e.g., sodium dodecyl sulfate (SDS), electrophoresis, hydrodynamic pressure, ultrasonic vibration, solute contrasts, microwave radiation, vascular circulation, and the like. In some instances, clearing is performed using a solvent that does not quench fluorescent proteins. Examples of organic solvents that are known to quench fluorescent proteins include tetrahydrofuran, hexane, benzylalcohol/benzylbenzoate (BABB), and dibenzyl ether. Accordingly, in order to preserve the fluorescence of various proteins, in some embodiments clearing is conducted using solvents other than those listed above, e.g., is conducted using non-organic solvents.

In some instances, clearing is conducted using an ionic surfactant, e.g., SDS, in order to expedite the clearing process by actively transporting charged ionic micelles out of the specimen that is being cleared. Clearing may be performed in any convenient buffer that is compatible with the selected clearance method, e.g., saline, phosphate buffer, phosphate buffered saline (PBS), sodium borate buffer, boric acid buffer, citric acid buffer, etc., as known in the art, and will typically take about 1-10 days per centimeter thickness of specimen, i.e., usually about 1 day, in some instances 2 days, sometimes 5 days, and typically no more than 10 days per cubic centimeter. Optimal time may be readily determined by visual inspection of the specimen for clarity.

After clearing, a sample will generally be substantially free of lipids. By "substantially free of lipids" is meant that the original amount of lipids present in the sample before clearing has been reduced by approximately 70% or more, such as by 75% or more, such as by 80% or more, such as by 85% or more, such as by 90% or more, such as by 95% or more, such as by 99% or more, such as by 100%.

Tissue specimens suitable for use with the methods and systems described herein generally include any type of tissue specimens collected from living or dead subjects, such as, e.g., biopsy specimens and autopsy specimens. Tissue specimens may be collected and processed using the methods and systems described herein and subjected to microscopic analysis immediately following processing, or may be preserved and subjected to microscopic analysis at a future time, e.g., after storage for an extended period of time. In some embodiments, the methods described herein may be used to preserve tissue specimens in a stable, accessible and fully intact form for future analysis. For example, tissue specimens, such as, e.g., human brain tissue specimens, may be processed as described above and cleared to remove a plurality of cellular components, such as, e.g., lipids, and then stored for future analysis. In some embodiments, the methods and systems described herein may be used to analyze a previously-preserved or stored tissue specimen. For example, in some embodiments a previously-preserved tissue specimen that has not been subjected to the CLARITY process may be processed and analyzed as described herein.

In some instances, no further manipulation of the specimen will be necessary for microscopic analysis. For example, the specimen may comprise biomolecules that can be directly visualized by microscopy. By "biomolecules" it is generally meant proteins, lipids, steroids, nucleic acids, etc. within a tissue or cell. One example of this would be if the organism that was the source of the specimen expressed a protein that possesses the ability to fluoresce, i.e. a "fluorescent protein", or "FP". By "fluoresce" is meant to absorb energy at one wavelength and emit it at another wavelength. For example, a green fluorescent protein (GFP) refers to a polypeptide that has a peak in the emission spectrum at 510 nm or about 510 nm. A variety of FPs that emit at various wavelengths are known in the art. FPs of interest include, but are not limited to, a green fluorescent protein (GFP), yellow fluorescent protein (YFP), orange fluorescent protein (OFP), cyan fluorescent protein (CFP), blue fluorescent protein (BFP), red fluorescent protein (RFP), far-red fluorescent protein, or near-infrared fluorescent protein. As used herein, Aequorea GFP refers to GFPs from the genus Aequorea and to mutants or variants thereof. Such variants and GFPs from other species, such as Anthozoa reef coral, Anemonia sea anemone, Renilla sea pansy, Galaxea coral, Acropora brown coral, Trachyphyllia and Pectimidae stony coral and other species are well known and are available and known to those of skill in the art. Exemplary GFP variants include, but are not limited to BFP, CFP, YFP and OFP. Examples of florescent proteins and their variants include GFP proteins, such as Emerald (Invitrogen, Carlsbad, Calif.), EGFP (Clontech, Palo Alto, Calif.), Azami-Green (MBL International, Woburn, Mass.), Kaede (MBL International, Woburn, Mass.), ZsGreenl (Clontech, Palo Alto, Calif.) and CopGFP (Evrogen/Axxora, LLC, San Diego, Calif.); CFP proteins, such as Cerulean (Rizzo, Nat Biotechnol. 22(4):445-9 (2004)), mCFP (Wang et al., PNAS USA. 101(48):16745-9 (2004)), AmCyanl (Clontech, Palo Alto, Calif.), MiCy (MBL International, Woburn, Mass.), and CyPet (Nguyen and Daugherty, Nat Biotechnol. 23(3): 355-60 (2005)); BFP proteins such as EBFP (Clontech, Palo Alto, Calif.); YFP proteins such as EYFP (Clontech, Palo Alto, Calif.), YPet (Nguyen and Daugherty, Nat Biotechnol. 23(3):355-60 (2005)), Venus (Nagai et al., Nat. Biotechnol. 20(1):87-90 (2002)), ZsYellow (Clontech, Palo Alto, Calif.), and mCitrine (Wang et al., PNAS USA. 101(48):16745-9 (2004)); OFP proteins such as cOFP (Strategene, La Jolla, Calif.), mKO (MBL International, Woburn, Mass.), and mOrange; and others (Shaner N C, Steinbach P A, and Tsien R Y., Nat Methods. 2(12):905-9 (2005)). Another class of fluorescent proteins is the red fluorescent protein Discosoma RFP (DsRed) that has been isolated from the corallimorph Discosoma (Matz et al., Nature Biotechnology 17: 969-973 (1999)), and red or far-red fluorescent proteins from any other species, such as Heteractis reef coral and Actinia or Entacmaea sea anemone, as well as variants thereof RFPs include, for example, Discosoma variants, such as monomeric red fluorescent protein 1 (mRFP1), mCherry, tdTomato, mStrawberry, mTangerine (Wang et al., PNAS USA. 101(48):16745-9 (2004)), DsRed2 (Clontech, Palo Alto, Calif.), and DsRed-T1 (Bevis and Glick, Nat. Biotechnol., 20: 83-87 (2002)), Anthomedusa J-Red (Evrogen) and Anemonia AsRed2 (Clontech, Palo Alto, Calif.). Far-red fluorescent proteins include, for example, Actinia AQ143 (Shkrob et al., Biochem J. 392(Pt 3):649-54 (2005)), Entacmaea eqFP611 (Wiedenmann et al. Proc Natl Acad Sci USA. 99(18):11646-51 (2002)), Discosoma variants such as mPlum and mRasberry (Wang et al., PNAS USA. 101(48): 16745-9 (2004)), and Heteractis HcRed1 and t-HcRed (Clontech, Palo Alto, Calif.).

Additionally or alternatively, it may be desirable to contact the cells and intracellular structures of the specimen with one or more macromolecules prior to microscopic analysis. For example, macromolecules may be provided that promote the visualization of particular cellular biomolecules, e.g., proteins, lipids, steroids, nucleic acids, etc. and sub-cellular structures. In some embodiments, the macromolecules are diagnostic. In some embodiments, the macromolecules are prognostic. In some embodiments, the macromolecules are predictive of responsiveness to a therapy. In some embodiments, the macromolecules are candidate agents in a screen, e.g., a screen for agents that will aid in the diagnosis and/or prognosis of disease, in the treatment of a disease, and the like.

For example, specimens may be contacted with nucleic acid stains like DAPI and Hoechst, which bind the minor groove of DNA, thus labeling the nuclei of cells. Drugs or toxins that bind specific cellular structures and have been derivatized with a fluorescent reporter may be employed, e.g., fluorescently labelled-phalloidin, which is used to stain actin fibers in mammalian cells. There are many fluorescent reported molecules, called fluorophores or fluorochromes such as fluorescein, Alexa Fluors or DyLight 488, which can be chemically linked to molecules which bind the target biomolecules of interest within the sample.

As another example, the specimen may be contacted with one or more polypeptides, e.g. antibodies, labeled peptides, and the like, that are specific for and will bind to particular cellular biomolecules for either direct or indirect labeling by color or immunofluorescence. By immunofluorescence it is meant a technique that uses the highly specific binding of an antibody to its antigen or binding partner in order to label specific proteins or other molecules within the cell. A sample is treated with a primary antibody specific for the biomolecule of interest. A fluorophore can be directly conjugated to the primary antibody or peptide. Alternatively a secondary antibody, conjugated to a detection moiety or fluorophore, which binds specifically to the first antibody can be used. See, for example, Buchwalow and Bocker. Immunohistochemistry: Basics and Methods, Springer-Verlag, Berlin Heidelberg 2010, and Hayat, M. A. Microscopy, Immunohistochemistry, and Antigen Retrieval Methods for Light and Electron Microscopy. Kluwar Academic Publishers, New York 2002, for examples of protocols that may be followed. Peptides that are specific for a target cellular biomolecule and that are conjugated to a fluorophor or other detection moiety may also be employed.

Another example of a class of agents that may be provided as macromolecules is nucleic acids. For example, a specimen may be contacted with an antisense RNA that is complementary to and specifically hybridizes to a transcript of a gene of interest, e.g., to study gene expression in cells of the specimen. As another example, a specimen may be contacted with a DNA that is complementary to and specifically hybridizes to genomic material of interest, e.g., to study genetic mutations, e.g., loss of heterozygosity, gene duplication, chromosomal inversions, and the like. The hybridizing RNA or DNA is conjugated to detection moieties, i.e. agents that may be either directly or indirectly visualized microscopically. Examples of in situ hybridization techniques may be found at, for example, Harris and Wilkinson. In situ hybridization: Application to developmental biology and medicine, Cambridge University Press 1990; and Fluorescence In Situ Hybridization (FISH) Application Guide. Liehr, T, ed., Springer-Verlag, Berlin Heidelberg 1990.

As another example, the specimen may be contacted with small molecules. For example, if the specimen comprises β-galactosidase or alkaline phosphatase, it may be desirable to visualize cells and regions of the tissue expressing these proteins. Towards this end, a specimen may be contacted with substrates for β-galactosidase (e.g. X-gal, 4-Trifluoromethylumbelliferyl-β-D-galactopyranoside (TFMU-Gal), Resorufin β-D-galactopyranoside (Res-gal), 4-Methylumbelliferyl β-D-galactopyranoside (MUG), di-β-D-galactopyranoside (FDG), Carboxyumbelliferyl β-D-galactopyranoside (CUG)) or for alkaline phosphatase (e.g. nitro-blue tetrazolium (NBT)/5-bromo-4-chloro-3'-indolylphosphate (BCIP)) and other reagents that allow for visualization of β-galactosidase or alkaline phosphatase activity. As another example, it may be desirous to visualize the dendritic arbors and spins of neurons in, e.g., a CNS specimen. To do so, the specimen may be exposed to chemicals used in Golgi-Cox impregnation, e.g., 3% potassium bichromate followed by a 2% silver nitrate solution.

In some instances, the biomolecules that are targeted by the provided macromolecules are endogenous to the cell. In other instances, the macromolecules may be provided to the specimen to target/visualize biomolecules that were ectopically provided to the cells of the specimen, e.g. agents that were introduced to the specimen in vivo or ex vivo to label certain cell populations or subcellular structures. For example, stereotactic surgery is often used in the field of neuroscience to provide biomolecules such as proteins, viruses, chemicals to neural tissue that label, or "trace", the projections and/or the connectivity of subsets of neurons in vivo or ex vivo. In this technique, a needle comprising a labeling macromolecule is lowered into CNS tissue at a precise location and the labeling molecule is released into the tissue. The molecule will fill the neurons in the vicinity of the injection site and, depending on the type of macromolecule delivered, may be transported across synapses to label their efferent targets ("anterograde tracing") and/or across dendrites to label the afferent neurons from which they are receiving signals ("retrograde tracing"). Examples of agents that may be used to label neurons stereotactically are well known in the art, including, for example, nucleic acids that encode fluorescent proteins; viral tracers, e.g. Herpes simplex virus type1 (HSV) and the Rhabdoviruses; wheat-germ agglutinin (WGA); *Phaseolus vulgaris* leucoagglutinin (PHA-L); horseradish peroxidase-conjugated lectins; biotinylated dextran amines (BDA); cholera toxin B; NEUROBIOTIN Tracer® (Vector labs). Specimens labeled in this way may be contacted with macromolecules, e.g. polypeptides or chemicals, that promote the visualization of these ectopically provided labels.

In some instances, the macromolecules that are used to visualize the cellular biomolecules or subcellular structures are passively transported into the specimen. In other words, the macromolecules diffuse into the specimen. In other instances, the macromolecules are actively transported into the specimen, e.g. by electroporation, hydrodynamic pressure, ultrasonic vibration, solute contrasts, microwave radiation, vascular circulation, or the like. In some embodiments, the specimen is contacted with the macromolecules after the specimen has been cleared. In other embodiments, the hydrogel-embedded specimen may be contacted with the macromolecules prior to clearing the specimen. In such embodiments, contact with the macromolecules may be facilitated by permeabilizing the specimen, that is, changing the properties of the specimen to improve the permeability of the specimen to macromolecules. By a "permeabilized" specimen it is meant that about 50% or more of the macromolecules applied to the specimen will penetrate to the deepest regions of the specimen, e.g. 60% or more of the macromolecules, 70% or more of the macromolecules, or 80% or more of the macromolecules, in some instances 85% or more of the macromolecules, 90% or more of the macromolecules, or 95% or more of the macromolecules, for example 98% or more of the macromolecules, e.g. 100% of the macromolecules will pass through the specimen. Permeabilization of the specimen, and of the cells therein, may be achieved by any of the protocols discussed above for the removal of cellular components, e.g. lipids, from the specimen or as known in the art for permeabilizing cells.

To microscopically visualize specimens prepared by the subject methods, in some embodiments the specimen is embedded in a mounting medium. Mounting medium is typically selected based on its suitability for the reagents used to visualize the cellular biomolecules, the refractive index of the specimen, and the microscopic analysis to be performed. For example, for phase-contrast work, the refractive index of the mounting medium should be different from the refractive index of the specimen, whereas for bright-field work the refractive indexes should be similar. As another example, for epifluorescence work, a mounting medium should be selected that reduces fading, photobleaching or quenching during microscopy or storage. In certain embodiments, a mounting medium or mounting solution may be selected to enhance or increase the optical clarity of the cleared tissue specimen. Nonlimiting examples of suitable mounting media that may be used include glycerol, CC/Mount™, Fluoromount™ Fluoroshield™, ImmunHistoMount™, Vectashield™, Permount™, Acrytol™, CureMount™, FocusClear™, or equivalents thereof.

In some instances, the hydrogel-embedded specimen is permanently mounted. In other words, once mounted in mounting medium, the hydrogel-embedded specimen cannot be removed for further manipulation. In other instances, the specimen is temporarily, or reversibly, mounted. In other words, the hydrogel-embedded specimen may be removed from the mounting medium and re-stained after microscopy to visualize alternative/additional biomolecules or subcellular structures. In such instances, macromolecules that were previously added to the specimen, e.g. to visualize certain biomolecules, may be removed after microscopic analysis by, e.g., exposure to organic solvents such as xylenes, ethanol or methanol, exposure to detergents such as sodium dodecyl sulfate (SDS), saponin, Triton X-100 and Tween-20, electrophoresis, hydrodynamic pressure, ultrasonic vibration, solute contrasts, microwave radiation, vascular circulation, and the like. The hydrogel-embedded specimen is then contacted with different macromolecules specific for other biomolecules or subcellular structures. As such, iterative staining may be performed on the same specimen.

Specimens prepared using the subject methods may be analyzed by any of a number of different types of microscopy, for example, optical microscopy (e.g. bright field, oblique illumination, dark field, phase contrast, differential interference contrast, interference reflection, epifluorescence, confocal, etc., microscopy), laser microscopy, electron microscopy, and scanning probe microscopy.

Bright field microscopy is the simplest of all the optical microscopy techniques. Sample illumination is via transmitted white light, i.e. illuminated from below and observed from above. Limitations include low contrast of most biological samples and low apparent resolution due to the blur of out of focus material. The simplicity of the technique and the minimal sample preparation required are significant advantages.

In oblique illumination microscopy, the specimen is illuminated from the side. This gives the image a 3-dimensional appearance and can highlight otherwise invisible features. A more recent technique based on this method is Hoffmann's modulation contrast, a system found on inverted microscopes for use in cell culture. Though oblique illumination suffers from the same limitations as bright field microscopy (low contrast of many biological samples; low apparent resolution due to out of focus objects), it may highlight otherwise invisible structures.

Dark field microscopy is a technique for improving the contrast of unstained, transparent specimens. Dark field illumination uses a carefully aligned light source to minimize the quantity of directly-transmitted (unscattered) light entering the image plane, collecting only the light scattered by the sample. Dark field can dramatically improve image contrast (especially of transparent objects) while requiring little equipment setup or sample preparation. However, the technique suffers from low light intensity in final image of many biological samples, and continues to be affected by low apparent resolution.

Phase contrast is an optical microscopy illumination technique that converts phase shifts in light passing through a transparent specimen to brightness changes in the image. In other words, phase contrast shows differences in refractive index as difference in contrast. The phase shifts themselves are invisible to the human eye, but become visible when they are shown as brightness changes.

In differential interference contrast (DIC) microscopy, differences in optical density will show up as differences in relief. The system consists of a special prism (Nomarski prism, Wollaston prism) in the condenser that splits light in an ordinary and an extraordinary beam. The spatial difference between the two beams is minimal (less than the maximum resolution of the objective). After passage through the specimen, the beams are reunited by a similar prism in the objective. In a homogeneous specimen, there is no difference between the two beams, and no contrast is being generated. However, near a refractive boundary (e.g. a nucleus within the cytoplasm), the difference between the ordinary and the extraordinary beam will generate a relief in the image. Differential interference contrast requires a polarized light source to function; two polarizing filters have to be fitted in the light path, one below the condenser (the polarizer), and the other above the objective (the analyzer).

Another microscopic technique using interference is interference reflection microscopy (also known as reflected interference contrast, or RIC). It is used to examine the adhesion of cells to a glass surface, using polarized light of a narrow range of wavelengths to be reflected whenever there is an interface between two substances with different refractive indices. Whenever a cell is attached to the glass surface, reflected light from the glass and that from the attached cell will interfere. If there is no cell attached to the glass, there will be no interference.

A fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" refers to any microscope that uses fluorescence to generate an image, whether it is a more simple set up like an epifluorescence microscope, or a more complicated design such as a confocal microscope, which uses optical sectioning to get better resolution of the fluorescent image.

Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity—so long exposures are often required. As only one point in the sample is illuminated at a time, 2D or 3D imaging requires scanning over a regular raster (i.e., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples.

In single plane illumination microscopy (SPIM), also known as light sheet microscopy, only the fluorophores in the focal plane of the detection objective lens are illuminated. The light sheet is a beam that is collimated in one and focused in the other direction. Since no fluorophores are excited outside the detectors' focal plane, the method also provides intrinsic optical sectioning. Moreover, when compared to conventional microscopy, light sheet methods exhibit reduced photobleaching and lower phototoxicity, and often enable far more scans per specimen. By rotating the specimen, the technique can image virtually any plane with multiple views obtained from different angles. For every angle, however, only a relatively shallow section of the specimen is imaged with high resolution, whereas deeper regions appear increasingly blurred.

Super-resolution microscopy is a form of light microscopy. Due to the diffraction of light, the resolution of conventional light microscopy is limited as stated by Ernst Abbe in 1873. A good approximation of the resolution attainable is the FWHM (full width at half-maximum) of the point spread function, and a precise widefield microscope with high numerical aperture and visible light usually reaches a resolution of ~250 nm. Super-resolution techniques allow the capture of images with a higher resolution than the diffraction limit. They fall into two broad categories, "true" super-resolution techniques, which capture information contained in evanescent waves, and "functional" super-resolution techniques, which use experimental techniques and known limitations on the matter being imaged to reconstruct a super-resolution image.

Laser microscopy uses laser illumination sources in various forms of microscopy. For instance, laser microscopy focused on biological applications uses ultrashort pulse lasers, or femtosecond lasers, in a number of techniques including nonlinear microscopy, saturation microscopy, and multiphoton fluorescence microscopy such as two-photon excitation microscopy (a fluorescence imaging technique that allows imaging of living tissue up to a very high depth, e.g. one millimeter)

In electron microscopy (EM), a beam of electrons is used to illuminate a specimen and produce a magnified image. An electron microscope has greater resolving power than a light-powered optical microscope because electrons have wavelengths about 100,000 times shorter than visible light (photons). They can achieve better than 50 μm resolution and magnifications of up to about 10,000,000× whereas ordinary, non-confocal light microscopes are limited by diffraction to about 200 nm resolution and useful magnifications below 2000×. The electron microscope uses electrostatic and electromagnetic "lenses" to control the electron beam and focus it to form an image. These lenses are analogous to but different from the glass lenses of an optical microscope that form a magnified image by focusing light on or through the specimen. Electron microscopes are used to observe a wide range of biological and inorganic specimens including microorganisms, cells, large molecules, biopsy samples, metals, and crystals. Industrially, the electron microscope is often used for quality control and failure analysis. Examples of electron microscopy include Transmission electron microscopy (TEM), Scanning electron microscopy (SEM), reflection electron microscopy (REM), Scanning transmission electron microscopy (STEM) and low-voltage electron microscopy (LVEM).

Scanning probe microscopy (SPM) is a branch of microscopy that forms images of surfaces using a physical probe that scans the specimen. An image of the surface is obtained by mechanically moving the probe in a raster scan of the specimen, line by line, and recording the probe-surface interaction as a function of position. Examples of SPM include atomic force microscopy (ATM), ballistic electron emission microscopy (BEEM), chemical force microscopy (CFM), conductive atomic force microscopy (C-AFM), electrochemical scanning tunneling microscope (ECSTM), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM).

Reagents and Kits

Also provided are reagents and kits thereof for practicing one or more of the above-described methods. Reagents and kits may include one or more of the following: fixative; hydrogel subunits; clearing reagents; detection macromolecules, e.g., labeled and or un-labeled antibodies, nucleic acid probes (oligonucleotides, vectors, etc.), chemicals, etc.; buffers, e.g. buffer for fixing, washing, clearing, and/or staining specimens; mounting medium; embedding molds; dissection tools; etc. The subject reagents and kits thereof may vary greatly.

Also provided are specimens that have been prepared by the subject methods for use in, for example, studying tissue at the cellular and subcellular level. For example, fixed and polymerized specimens, or specimens that have been fixed, polymerized, and cleared, are provided for use in studying the expression of genes of interest, for screens to identify candidate agents that target cells and/or subcellular structures of interest, etc. Such prepared specimens may also be provided as a positive control in one of the kits or systems as described herein.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, digital storage medium, etc., on which the information has been recorded. Yet another means that may be present is a website address which may be used via the Internet to access the information at a removed site. Any convenient means may be present in the kits.

Devices and Systems

Also included are devices for performing aspects of the subject methods. The subject devices may include, for example, electrophoresis apparatus, ultrasounds, microwaves, needles, tubing, perfusion pumps, etc., for fixing, clearing, and/or staining specimens.

One device of particular interest is an electrophoresis device suitable for use in removing cellular components from a specimen, e.g., cellular components that are not crosslinked to the hydrogel network. By "electrophoresis" it is meant the application of an electric field to a sample, e.g., to a biological sample. Electrophoresis is most commonly used to mobilize biological macromolecules, e.g., nucleic acids, proteins, in a sample to separate and analyze those macromolecules. Numerous electrophoretic techniques have been developed including capillary electrophoresis, gel electrophoresis, paper electrophoresis, and immunoelectrophoresis. For example, in gel electrophoresis, a hydrogel is formed using compounds such as agarose or polyacrylamide. A mixture containing the desired macromolecules is placed (or loaded) onto one end of the gel, and the gel is then placed in contact with a liquid buffer. This liquid buffer contains salts, which, when dissolved, form ions within the buffer. Biological molecules are typically charged, for example when contacted with electrophoresis buffer. For example, DNA is negatively charged in common electrophoresis buffers due to the phosphate groups in its backbone. Therefore, when electric current is applied to the ends of the gel, the biological molecules move through the gel from one end to the other. Examples of electrophoresis devices and methods of gel electrophoresis may be found in, for example, U.S. Pat. Nos. 3,129,158, 3,208,929, 3,346,479, 3,375,187, 3,616,454, 3,616,457, 3,616,454, 3,616,457, 3,563,880, 3,576,727, 3,674,678, 3,865,712, 4,088,561, 4,151,065, 4,292,161, 4,339,327, 4,375,401, 4,415,418, 4,479,861, and 4,588,491; and Martin, Robin. Gel electrophoresis: nucleic acids. BIOS Scientific, 1996; Hames, B. D. Gel Electrophoresis of Proteins: A Practical Approach, Oxford University Press 1998; and Burmeister, M. and Ulanovsky, L. Pulsed-field Gel Electrophoresis, The Humana Press Inc. 1992, the disclosures of which are incorporated herein by reference.

Electrophoresis devices suitable for use in the subject methods will generally comprise an electrophoresis chamber into which a buffer solution and the hydrogel-embedded specimen may be placed. See, for example, FIG. 2 and FIG. 8. The electrophoresis chamber may generally be any suitable size to accommodate a hydrogel-embedded sample of interest, and may be constructed of any material that will retain solution within the chamber, for example glasses and plastics, such as, for example, acrylics, polycarbonates, polystyrenes, polymethyl methacrylates, polyethylene, polyfluoroethylene, polypropylene, polyurethane, polyethylene terephthalate, polytetrafluoroethylene and the like. In some embodiments, a chamber may be molded or machined or otherwise formed from a resin or hard plastic, as appropriate for particular applications. In certain embodiments, an electrophoresis chamber may further comprise a component that is configured to support a hydrogel-embedded sample, such as, e.g., a platform, within the electrophoresis chamber.

In some embodiments, an electrophoresis device may include a lid that fits over the electrophoresis chamber to close the chamber. Lids in accordance with embodiments of the invention may include a seal that forms a liquid-tight and/or air-tight seal with the body of the electrophoresis chamber when the lid is coupled to the chamber. In some embodiments, one or more sealing components may be attached to the lid, attached to the chamber, or attached to both the lid and the chamber. When the lid is coupled to the chamber, the sealing components may form a liquid and/or air-tight seal.

Electrophoresis devices in accordance with some embodiments of the invention may comprise two or more electrodes of opposite polarity (i.e. "anode" (negatively charged) and at least one "cathode" (positively charged)) operably associated with the electrophoresis chamber to which an electric current may be applied to create an electric field within the chamber. The electrodes may be constructed of any material that will result in an electric field being established upon the application of an electric current to the electrodes, and may be configured within the chamber and relative to the site where the specimen is to be placed in any convenient way that will promote the establishment of an electric field across a specimen positioned therein, for example as well known in the art of nucleic acid or protein electrophoresis. See, for example, U.S. Pat. Nos. 3,129,158, 3,208,929, 3,346,479, 3,375,187, 3,616,454, 3,616,457, 3,616,454, 3,616,457, 3,563,880, 3,576,727, 3,674,678, 3,865,712, 4,088,561, 4,151,065, 4,292,161, 4,339,327, 4,375,401, 4,415,418, 4,479,861, and 4,588,491; and Martin, Robin. Gel electrophoresis: nucleic acids. BIOS Scientific, 1996; Hames, B. D. Gel Electrophoresis of Proteins: A Practical Approach. Oxford University Press 1998; and Burmeister, M. and Ulanovsky, L. Pulsed-field Gel Electrophoresis, The Humana Press Inc. 1992. For example, the electrodes may be configured within the chamber so as to substantially flank the specimen.

Figure 8:
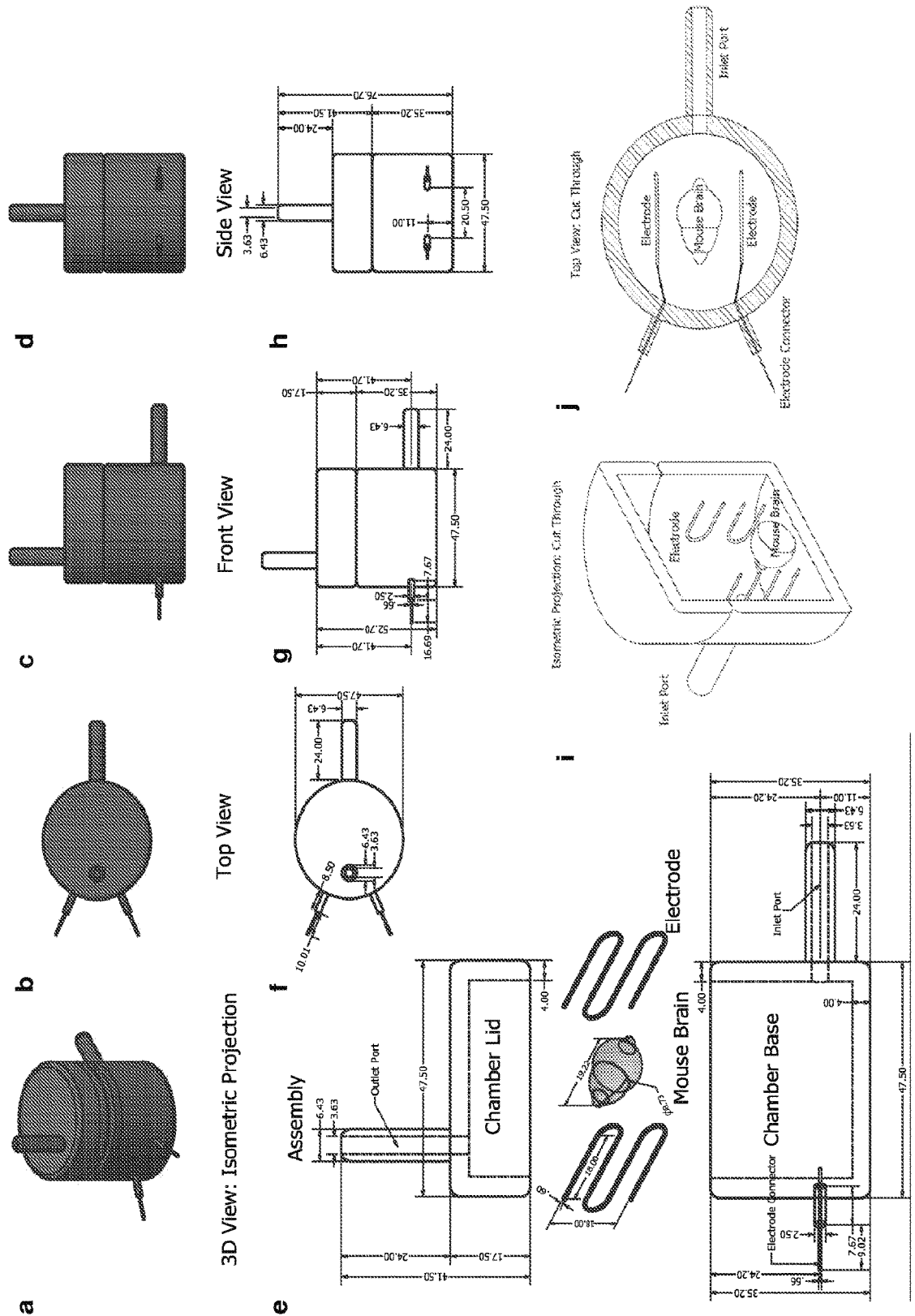
FIG. 8 is a collection of drawings showing an example of an ETC chamber design. Indicated dimensions are in millimeters.

In some embodiments, one or more of the electrodes may comprise an extension component that is used to enlarge the size of the electric field that is generated between the electrodes. For example, in certain embodiments, an electrode may comprise an extension component in the form of a serpentine portion of the electrode the doubles back on itself to form a plurality of S-shaped bends. An example of an electrode comprising a serpentine extension component can be seen in FIG. 2, Panel c (reference numbers 103a and 103b). The extension component enlarges the size of the electric field that is generated when a voltage is applied to the electrodes so that an entire three-dimensional tissue specimen can be placed inside the electric field. The length and width of the extension component can be adjusted as needed to accommodate tissue specimens of various dimensions. For example, in certain embodiments the length and the width of an electrode comprising an extension component are approximately equal, as depicted in FIG. 8, Panel e.

In certain embodiments, an electrophoresis chamber may be partitioned by, e.g., a solid divider or by air into two distinct regions, where each region comprises one electrode in a buffer, and the specimen is positioned within the buffer such that the specimen spans, or straddles the two regions, such that the electric field created by the electrodes is created through the specimen. In some instances, the chamber may comprise a platform or support structure, upon or into which the hydrogel-embedded specimen is placed, e.g., a platform between two electrodes, a platform that spans regions of the chamber comprising the electrodes, etc.

The electrophoresis apparatus may be operably linked to a power source from which voltage may be applied to the electrodes. In some instances, the power source may be separate from the electrophoresis apparatus, i.e. the electrophoresis apparatus may be a separate module from the power source. In other instances, the power source may be integrated into the electrophoresis apparatus, i.e., the electrophoresis apparatus will comprise the power source.

In some instances, it may be desirable to replace or recirculate buffer in the electrophoresis chamber. By "circulated" or "recirculated" buffer it is meant that buffer is removed from the chamber and then returned to the chamber, for example, after passing through a cooling unit (refrigeration unit, ice bath, etc.), a heating unit, a filter, etc. By "replaced" is meant that buffer is removed from the chamber and fresh buffer is added in its place. For example, it may be desirable to control the temperature of the buffer inside the electrophoresis chamber (e.g., to prevent the chamber from reaching temperatures that might cause the hydrogel to depolymerize or the biomolecules in the specimen to denature, e.g., 35° C. or more, 40° C. or more, or 50° C. or more, 60° C. or more, 70° C. or more, 80° C. or more, 90° C. or more, or 100° C. or more); to remove macromolecules from the buffer as they exit the specimen; to vary the ionic strength of the buffer; etc. Towards this end, the electrophoresis apparatus may optionally comprise one or more ports through which buffer may enter and/or exit the chamber. In some instances, the chamber may comprise two or more ports, e.g. a first port through which buffer enters the chamber and a second port through which buffer exits the chamber.

Buffer may be added/removed/recirculated/replaced by the use of the one or more ports and optionally, tubing, pumps, valves, or any other suitable fluid handling and/or fluid manipulation equipment, for example, tubing that is removably attached or permanently attached to one or more components of a device. For example, a first tube having a first and second end may be attached to a first port and a second tube having a first and second end may be attached to a second port, where the first end of the first tube is attached to the first port and the second end of the first tube is operably linked to a receptacle, e.g. a cooling unit, heating unit, filtration unit, waste receptacle, etc.; and the first end of the second tube is attached to the second port and the second end of the second tube is operably linked to a receptacle, e.g. a cooling unit, beaker on ice, filtration unit, waste receptacle, etc.

As another example, one tube having a first and second end may be removably attached to both a first and second port, i.e., the first end of the tube is removably attached to the first port and the second end of the tube is removably attached to the second port, where the tubing is operably linked to, for example, a refrigeration unit (e.g., the tubing passes through the unit), a filter (e.g. the tubing comprises a filter), a buffer reservoir (e.g. the tubing receives replacement buffer from a reservoir via, e.g., a splitter), etc. In some instances, the tubing will also be operably connected to a pump, e.g. a peristaltic pump, an electro-osmotic pump, an oscillatory pump, a diaphragm pump etc., that will facilitate the movement of liquid through the tubing, facilitate the addition/removal/recirculation of buffer from the electrophoresis chamber, etc. In this way, the electrophoresis apparatus may be operably connected to a cooling unit, heating unit, filtration unit, buffer reservoirs/receptacles, pump, etc. In some embodiments, a refrigeration unit, heating unit, filtration unit, buffer reservoirs/receptacles, pump, etc. will be integrated into the electrophoresis apparatus. In other words, the electrophoresis apparatus may comprise the refrigeration unit, heating unit, filtration unit, buffer reservoirs/receptacles, pump, etc. In other embodiments, the refrigeration unit, heating unit, filtration unit, buffer reservoirs/receptacles, pump, etc., may be a separate module from the electrophoresis apparatus.

Figure 2:
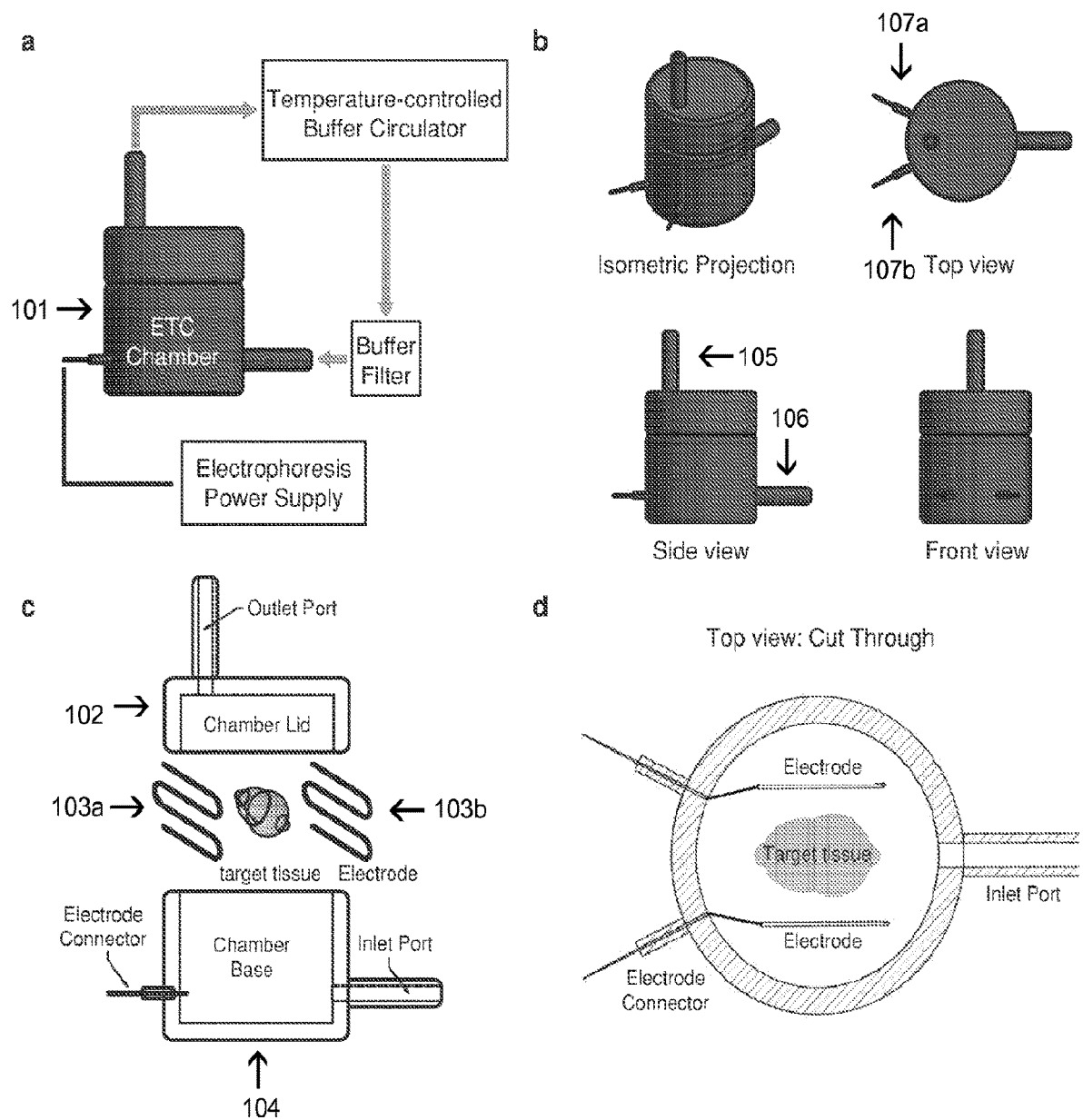
FIG. 2 is an illustration of an electrophoretic tissue clearing (ETC) device and related instrumentation.

Turning now to FIG. 2, a representative electrophoretic tissue clearing device is shown. The example device 101 includes a lid 102, a first electrode 103a, a second electrode 103b, a base 104, an outlet port 105, an inlet port 106, a first electrode connector 107a and a second electrode connector 107b.

The present disclosure also provides systems for performing the subject methods. Systems may include one or more of the modules described herein, e.g. an electrophoresis apparatus, a power supply, a refrigeration unit, a heating unit, a pump, etc. Systems may also include any of the reagents described herein, e.g. fixative; hydrogel subunits; clearing reagents; detection macromolecules, e.g., antibodies, nucleic acid probes (oligonucleotides, vectors, etc.), chemicals, etc.; buffers, e.g., buffer for fixing, washing, clearing, and/or staining specimens; mounting medium; embedding molds; etc. Systems in accordance with certain embodiments may also include a microscope and/or related imaging equipment, e.g., camera components, digital imaging components and/or image capturing equipment, computer processors configured to collect images according to one or more user inputs, and the like.

Applications

Using the subject methods, reagents, kits, systems and devices, the ordinarily skilled artisan will be able to prepare any biological tissue for microscopic analysis. Methods, reagents, kits, systems and devices may be used to prepare a specimen from any plant or animal, including but not limited to transgenic animals, e.g., vertebrate or invertebrate, e.g. insect, worm, xenopus, zebrafish, mammal, e.g. equine, bovine, ovine, canine, feline, murine, rodent, non-human primate or human. Tissue specimens may be collected from living subjects (e.g., bipsy samples) or may be collected from dead subjects (e.g., autopsy or necrospsy samples). The specimens may be of any tissue type, e.g. hematopoietic, neural (central or peripheral), glial, mesenchymal, cutaneous, mucosal, stromal, muscle (skeletal, cardiac, or smooth), spleen, reticulo-endothelial, epithelial, endothelial, hepatic, kidney, pancreatic, gastrointestinal, pulmonary, fibroblast, and other cell types. In some instances, the specimen is the entire organism, e.g. a worm, an insect, a zebrafish. In other instances, the specimen is a whole organ, e.g., the whole brain of a rodent. In other instances, the specimen is a portion of an organ, i.e. a biopsy, e.g. a biopsy of a transplanted tissue. The specimen may be freshly isolated or preserved, e.g. snap frozen. In some embodiments, the specimen may be a previously preserved specimen, such as, e.g., a preserved specimen from a tissue bank, e.g., a preserved specimen of a human brain obtained from a tissue collection program. In some instances, a specimen may be from a subject known to suffer from a specified disease or condition, such as, e.g., a sample of brain tissue from an autistic human. In other instances, a sample may be from a "normal" subject that does not suffer from a specific disease or condition. In some instances, a sample may be from a transgenic subject, such as, e.g., a transgenic mouse.

Because the cells of the specimen are crosslinked to a hydrogel that physically supports the ultrastructure of the tissue, cellular components, e.g. lipids, that normally provide structural support but that hinder visualization of subcellular proteins and molecules may be removed while preserving the 3-dimensional architecture of the cells and tissue. This removal renders the interior of biological specimen substantially permeable to light and/or macromolecules, allowing the interior of the specimen, e.g. cells and subcellular structures, to be microscopically visualized without time-consuming and disruptive sectioning of the tissue. The procedure is also more rapid than procedures commonly used in the art, as clearance and permeabilization, typically performed in separate steps, may be combined in a single step of removing cellular components. Additionally, the specimen can be iteratively stained, unstained, and re-stained with other reagents for comprehensive analysis.

The subject methods find many uses. For example, the subject methods may be applied to preparing specimens for the study of the connectivity of the central nervous system. "Connectivity" as used herein generally means the connections between neurons, and includes connections at the single cell level, e.g., synapses, axon termini, dendritic spines, etc., as well as connections between groups of neurons and regions of the CNS as major axon tracts, e.g., corpus callosum (CC), anterior commissure (AC), hippocampal commissure (HC), pyramidal decussation, pyramidal tracts, external capsule, internal capsule (IC), cerebral peduncle (CP), etc. A whole brain and/or spinal cord specimen or region thereof (e.g. cerebrum (i.e. cerebral cortex), cerebellum (i.e. cerebellar cortex), ventral region of the forebrain (e.g. striatum, caudate, putamen, globus pallidus, nucleus accumbens; septal nuclei, subthalamic nucleus); regions and nuclei of the thalamus and hypothalamus; regions and nuclei of the deep cerebellum (e.g dentate nucleus, globose nucleus, emboliform nucleus, fastigial nucleus) and brainstem (e.g. substantia nigra, red nucleus, pons, olivary nuclei, cranial nerve nuclei); and regions of the spine (e.g. anterior horn, lateral horn, posterior horn)) may be prepared post-mortem by the subject methods and the connectivity of the neurons therein microscopically analyzed, e.g. obtained, stored, rendered, used, and actuated, e.g. to provide the full connectivity of a brain, e.g. a human brain, after death. Such studies will contribute greatly to the understanding of how the brain develops and functions in health and during disease, and of the underpinnings of cognition and personality.

As another example, the subject methods may be employed to evaluate, diagnose or monitor a disease. "Diagnosis" as used herein generally includes a prediction of a subject's susceptibility to a disease or disorder, determination as to whether a subject is presently affected by a disease or disorder, prognosis of a subject affected by a disease or disorder (e.g., identification of cancerous states, stages of cancer, likelihood that a patient will die from the cancer), prediction of a subject's responsiveness to treatment for a disease or disorder (e.g., a positive response, a negative response, no response at all to, e.g., allogeneic hematopoietic stem cell transplantation, chemotherapy, radiation therapy, antibody therapy, small molecule compound therapy) and use of therametrics (e.g., monitoring a subject's condition to provide information as to the effect or efficacy of therapy). For example, a biopsy may be prepared from a cancerous tissue and microscopically analyzed to determine the type of cancer, the extent to which the cancer has developed, whether the cancer will be responsive to therapeutic intervention, etc.

As another example, a biopsy may be prepared from a diseased tissue, e.g. kidney, pancreas, stomach, etc., to determine the condition of the tissue, the extent to which the disease has developed, the likelihood that a treatment will be successful, etc. The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease. The terms "individual," "subject," "host," and "patient," are used interchangeably herein and refer to any mammalian subject for whom diagnosis, treatment, or therapy is desired, particularly humans. Examples of diseases that are suitable to evaluation, analysis, diagnosis, prognosis, and/or treatment using the subject methods and systems include, but are not limited to, cancer, immune system disorders, neuropsychiatric disease, endocrine/reproductive disease, cardiovascular/pulmonary disease, musculoskeletal disease, gastrointestinal disease, and the like.

Similarly, the subject methods may be used to monitor tissue grafts to determine how well the subject has accepted a transplanted organ/tissue, e.g. heart, kidney, liver, or other organ. In such instances, a biopsy of the transplanted organ may be prepared by the subject methods, and the specimen microscopically analyzed for, e.g., tissue integrity, tissue vascularization, the infiltration of immune cells, etc.

The subject methods may also be used to evaluate normal tissues, organs and cells, for example to evaluate the relationships between cells and tissues of a normal tissue specimen, e.g., a tissue specimen taken from a subject not known to suffer from a specific disease or condition. The subject methods may be used to investigate, e.g., relationships between cells and tissues during fetal development, such as, e.g., during development and maturation of the nervous system, as well as to investigate the relationships between cells and tissues after development has been completed, e.g., the relationships between cells and tissues of the nervous systems of a fully developed adult specimen. In some embodiments, the subject methods may be used on samples collected from transgenic animals to investigate the effects of genetic changes on the development and/or function of specific cells, tissues, and/or organs.

The subject methods also provide a useful system for screening candidate therapeutic agents for their effect on a tissue or a disease. For example, a subject, e.g. a mouse, rat, dog, primate, human, etc. may be contacted with a candidate agent, an organ or a biopsy thereof may be prepared by the subject methods, and the prepared specimen microscopically analyzed for one or more cellular or tissue parameters. Parameters are quantifiable components of cells or tissues, particularly components that can be accurately measured, desirably in a high throughput system. A parameter can be any cell component or cell product including cell surface determinant, receptor, protein or conformational or post-translational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values. Thus, for example, one such method may comprise detecting cellular viability, tissue vascularization, the presence of immune cell infiltrates, efficacy in altering the progression of the disease, etc. In some embodiments, the screen includes comparing the analyzed parameter(s) to those from a control, or reference, sample, e.g., a specimen similarly prepared from a subject not contacted with the candidate agent. Candidate agents of interest for screening include known and unknown compounds that encompass numerous chemical classes, primarily organic molecules, which may include organometallic molecules, inorganic molecules, genetic sequences, etc. Candidate agents of interest for screening also include nucleic acids, for example, nucleic acids that encode siRNA, shRNA, antisense molecules, or miRNA, or nucleic acids that encode polypeptides. An important aspect of the invention is to evaluate candidate drugs, including toxicity testing; and the like. Evaluations of tissue samples using the subject methods may include, e.g., genetic, transcriptomic, genomic, proteomic, and/or metabolomics analyses.

The subject methods may also be used to visualize the distribution of genetically encoded markers in whole tissue at subcellular resolution, for example, chromosomal abnormalities (inversions, duplications, translocations, etc.), loss of genetic heterozygosity, the presence of gene alleles indicative of a predisposition towards disease or good health, likelihood of responsiveness to therapy, ancestry, and the like. Such detection may be used in, for example, diagnosing and monitoring disease as, e.g., described above, in personalized medicine, and in studying paternity.

Materials and Methods

The following materials and methods were used in the examples below.

CLARITY Process for Mouse Brain:

Adult mice (4-12 weeks old) were anesthetized with Beuthenasia-D and perfused transcardially with a mixture of 4 wt % paraformaldehyde/4% acrylamide (wt/vol)/0.025% bis-acrylamide (wt/vol)/0.25% VA044 (wt/vol)/PBS. The brains were then extracted and incubated in the same solution at 4° C. for three days. In the next step, the temperature of the solution was increased to 37° C. to initiate polymerization. After three hours incubation at 37° C., the hydrogel-embedded brains were placed in an electrophoresis chamber. While circulating sodium borate buffer (200 mM, pH 8.5) containing 4% SDS (wt/vol) through the chamber, 10-40V was applied across the brains at 50° C. for two days. After clearing, the brains were incubated in PBS buffer at 37° C. for two days to remove SDS from the brain. To make 1 mm-thick coronal blocks of mouse brain for immunostaining, the hydrogel-embedded and cleared brains were cut into 1 mm-thick blocks using a mouse brain matrix (cat. no. 15003, Ted Pella, inc., Redding, Calif.). The blocks were then cleared by electrophoresis for one day as described above.

CLARITY Process for Postmortem Human Brain Tissue:

The frontal lobe (Brodmann's area 10) of postmortem human brain tissue (autism case, #AN13961; age, 7 years; sex, male; storage, 82 months in 10% formalin at room temperature) was sliced into 500 μm-thick blocks using a vibratome. The blocks were incubated in a mixture of 4 wt % paraformaldehyde/4% acrylamide (wt/vol)/0.025% bis-acrylamide (wt/vol)/0.25% VA044 (wt/vol)/PBS at 4° C. for one week. Next, the temperature of the solution was increased to 37° C. to initiate polymerization. After three hours of incubation at 37° C., the hydrogel-embedded tissues were placed in the custom-built electrophoresis chamber (see FIG. 2 and FIG. 8). While circulating sodium borate buffer (200 mM, pH 8.5) containing 4% SDS (wt/vol) through the chamber, 10-40V was applied across the tissues at 50° C. for one day. After clearing, the cleared tissues were incubated in PBS buffer at 37° C. for one day to remove SDS.

Immunostaining of the CLARITY-Processed Mouse Brain Tissues:

For GFP staining, the cleared 1 mm-thick block of Thy1-EYFP H line mouse (two months old) brain was incubated at 37° C. for two days in 0.1% Triton X-100 (wt/vol)/anti-GFP antibody conjugated with Alexa Fluor 594 (Cat. no. A21312, Invitrogen, Carlsbad, Calif., 1:50 dilution)/1M sodium borate buffer (pH 8.5) solution, followed by wash at 37° C. for one day with 0.1% Triton X-100 (wt/vol)/1M sodium borate buffer (pH 8.5). For the other staining, the cleared 1 mm-thick block of Thy1-EYFP H line mouse (two months old) was incubated at 37° C. for two days in 0.1% Triton X-100 (wt/vol)/primary antibody (dilution, 1:50-1:100)/1M sodium borate buffer (pH 8.5) solution, followed by wash at 37° C. for one day with 0.1% Triton X-100 (wt/vol)/1M sodium borate buffer (pH 8.5). The tissue was then incubated at 37° C. for one day in 0.1% Triton X-100 (wt/vol)/secondary antibody (dilution, 1:50-1:100)/1M sodium borate buffer (pH 8.5) solution, followed by wash at 37° C. for one day with 0.1% Triton X-100 (wt/vol)/1M sodium borate buffer (pH 8.5).

Immunostaining of the CLARITY-Processed Postmortem Human Brain Tissues:

The cleared 500 μm-thick blocks were incubated at 37° C. for one day in 0.1% Triton X-100 (wt/vol)/primary antibody (dilution, 1:50-1:100)/1M sodium borate buffer (pH 8.5)

solution, followed by wash at 37° C. for half day with 0.1% Triton X-100 (wt/vol)/1M sodium borate buffer (pH 8.5). The tissue was then incubated at 37° C. for one day in 0.1% Triton X-100 (wt/vol)/secondary antibody (dilution, 1:50-1: 100)/1M sodium borate buffer (pH 8.5) solution, followed by wash at 37° C. for half day with 0.1% Triton X-100 (wt/vol)/1M sodium borate buffer (pH 8.5).

Imaging of the CLARITY Processed Mouse Brain Tissues:

For imaging the intact Thy1-EYFP H line mouse brain, the cleared brain (three months old) was incubated in FocusClear™, a water-based immersion medium, for two days. The brain was then enclosed between two coverglass-bottom petri dishes. The dorsal half of the brain was first imaged (stack size=3.4 mm, step-size=10 μm) using a Leica SP5 system equipped with the 10× water-immersion objective (Leica HCX AOP L, NA=0.30, working distance=3.6) and 514 nm excitation. The mounted brain was then flipped and the ventral half was imaged in the same way.

To obtain the 3.4 mm-thick volume image visualizing from the cortex to the thalamus, the intact H line mouse brain was mounted as described and imaged using the 10× objective and 514 nm excitation (stack size=3.4 mm, step-size=2 μm).

The immunostained 1 mm-thick coronal blocks were incubated in FocusClear™ for one day and enclosed between the coverglass-bottom petri dish and slideglass. The mounted samples were imaged using the 10× objective and one-photon excitations (514 nm, 591 nm, and 654 nm).

Imaging of the CLARITY-Processed Postmortem Human Brain Tissue:

The cleared and immunostained tissues were incubated in FocusClear™ for one day and mounted as described above. The tissues were then imaged using the Leica SP5 system equipped with the 25× water-immersion objective (Leica HCX IRAPO L, NA=0.95, working distance=2.4) (stack size=500 μm, step-size=0.5 μm). Alexa Fluor 594 was excited with a 780 nm laser.

Protein Loss Measurement:

Six PFA-fixed adult mouse (four weeks old) brains (for 4% SDS, Scale, and Triton X-100 treatments) and two (four weeks old) PFA-fixed/hydrogel-embedded brains (for CLARITY) were cut into 1 mm-thick coronal blocks. One half of each PFA-fixed brain was weighed and placed in 2.5 ml of 4% SDS, ScaleU2 (a mixture of 4M urea and 30% glycerol) or 0.1% Triton X-100 solution. One half of each PFA-fixed/hydrogel-embedded brain was placed in 2.5 ml of 4% SDS solution. The tissues were allowed to clear for one week at 37° C. in the respective solutions and quantity of protein lost from tissue by diffusing into solution was measured using the BCA (bicinchoninic acid) protein assay; total protein in mouse brain estimated at 10 wt %.

Neurite Tracing:

Manual tracing of individual neurons was performed using Imaris software (Bitplane, Inc). Neurons whose cell bodies were located in the middle 150 μm of the z-stack were randomly sampled and chosen for tracing. The cell body was reconstructed semi-automatically through a user-defined threshold which included as much as the cell body as possible but less than 5 μm of any dendrite. All neurites originating from the cell body were traced manually in short segments in the "Surpass" mode, and each segment was automatically centered (with the opportunity for user corrections) before being connected. The number of interconnections between filaments of the same cell and the number of interconnections between a filament from the traced cell and that of any other cell were manually counted. Neurons exhibiting interesting structures were chosen non-randomly and traced using the same method described above.

Hydrogel Solution Preparation:

1. Combine and mix the following with special attention to temperature and safety precautions. Keep all components on ice at all times to prevent polymerization.

Caution: paraformaldehyde (PFA) is an irritant, sensitizer, carcinogen and toxin. Acrylamide is a potent neurotoxin, a respiratory and skin sensitizer, carcinogen, irritant, mutagen, teratogen and reproductive hazard. Many of the chemical constituents of hydrogels which could be used for CLARITY would fall into one or more of these categories. Therefore, to avoid skin contact or inhalation of monomers and/or crosslinkers (e.g. acrylamide or PFA), solution preparation and all subsequent handling of hydrogel solution and polymer must be conducted in a fume hood with personal protective equipment (PPE) including face shield, lab coat, gloves, and closed-toe shoes.

For 400 mL of Hydrogel Monomer Solution:

| Ingredient | Add: | Final Concentration |
|---|---|---|
| Acrylamide (40%) | 40 mL | 4% |
| Bis (2%) | 10 mL | 0.025% |
| VA-044 Initiator | 1 g | 0.25% |
| 10X PBS | 40 mL | 1X |
| 16% PFA | 100 mL | 4% |
| dH$_2$O | 210 mL | NA |
| Saponin (optional) | 200 mg | 0.05% |
| Total Volume | 400 mL | NA |

Saponin is a widely-used mild non-ionic surfactant often used to permeabilize cellular membranes in conventional immunohistochemistry. In CLARITY, saponin can be employed in the hydrogel monomer infusion process to facilitate diffusion of the hydrogel monomer and initiator into the tissue, particularly for samples in which cardiac perfusion is not feasible, such as postmortem human tissues and zebrafish brains. Saponin shortens incubation time required in the hydrogel monomer infusion process. However, bubbles may form that could be linked to saponin use, so routine saponin is not suggested.

2. Distribute 40 mL aliquots into 50 mL conical tubes on ice. Each tissue sample will require the use of one 40 mL tube: 20 mL for perfusion and the remaining 20 mL for sample embedding.

3. Seal tubes tightly and keep in secondary containment (on ice) before removing them from the hood. Transfer aliquots from ice to −20° C. Store these solutions at −20° C. until they are ready to be used. They can be stored at −20° C. indefinitely if all components were kept sufficiently cold during the preparation process.

Clearing Solution Preparation:

1. To avoid skin contact or inhalation, prepare solution in a fume hood in proper PPE. Paying special attention to safety, combine water, boric acid, and Sodium Dodecyl Sulfate (SDS) while stirring. Add NaOH until the pH has reached 8.5. This solution can be made, stored, and used at room temperature. Caution: SDS is a toxin and irritant to the skin and respiratory system.

For 10 L of Clearing Solution:

| Ingredient | Add: | Final Concentration |
|---|---|---|
| Boric Acid | 123.66 g | 200 mM |
| Sodium Dodecyl Sulfate | 400 g | 4% |

-continued

| Ingredient | Add: | Final Concentration |
|---|---|---|
| dH$_2$O | Fill to 10 L | NA |
| NaOH | To pH 8.5 | NA |
| Total Volume | 10 L | NA |

Transcardial Perfusion with Hydrogel Solution:
1. Prior to perfusing, thaw the frozen hydrogel monomer solution in the refrigerator or on ice.
2. When the solution is completely thawed and transparent (but still ice cold), gently invert to mix. Make sure that there is no precipitate, and avoid introducing any bubbles into the solution.
3. Prepare perfusion materials within a fume hood.
4. Deeply anesthetize adult mouse with Beuthanasia-D.
5. Perfuse the animal transcardially first with 20 mL of ice cold 1×PBS and then 20 mL of the ice cold hydrogel solution. Maintain a slow rate of perfusion (about 2 minutes for the 20 mL of each solution).
6. Immediately place the tissue (e.g. brain) in 20 mL of cold hydrogel solution in a 50 mL conical tube. Keep the sample in solution on ice until it can be moved to a 4° C. refrigerator.
7. Cover sample in aluminum foil if it contains fluorophores, and incubate at 4° C. for 2-3 days to allow for further diffusion of the hydrogel solution into the tissue.

Hydrogel Tissue Embedding:
1. De-gas the 50 mL conical tube containing your sample in the desiccation chamber (in a fume hood) to replace all of the gas in the tube with nitrogen (as oxygen impedes hydrogel formation), as follows:
   a. Place the 50 mL conical tube on a rack in the desiccation chamber.
   b. Twist the 50 mL conical tube open sufficiently to allow gas exchange.
   c. Turn on the nitrogen tank and adjust the control valve such that the inlet to the desiccation chamber fills with nitrogen gas.
   d. Switch the desiccation chamber valve from nitrogen gas flow to the vacuum.
   e. Turn on the vacuum pump. Verify that the chamber is under full vacuum by testing the chamber lid. Keep vacuum on for 10 minutes.
   f. Switch the vacuum off and slowly turn the valve to fill the chamber with nitrogen gas.
   g. Carefully open the chamber just enough to reach the tubes while purging with nitrogen gas. Taking great care to minimize exposure to air, and quickly and tightly close the sample tube.
2. Submerge the tube in 37° C. water bath in a 37° C. room or incubator on the rotator. Incubate for 3 hours or until solution has polymerized.
3. In a fume hood, extract the embedded sample from the gel (carefully take the sample out and remove extra gel pieces with gloved fingers). Hydrogel waste disposal should be conducted in accordance with all institutional, state and country regulations for hydrogel monomers and crosslinkers (e.g. acrylamide and PFA).
4. Wash the sample with 50 mL of clearing solution for 24 hours at room temperature to dialyze out extra PFA, initiator, and monomer. Wash the sample two more times with 50 ml for 24 hours each at 37° C. to further reduce residual PFA, initiator, and monomer. Take care to dispose of this waste solution carefully as a biohazard.

Electrophoretic Tissue Clearing (ETC):
1. Construct the ETC chamber.
   a. Place the sample in the chamber.
   b. Circulate the clearing solution through the chamber using the temperature controlled circulator, with 10-60V applied across the tissue (e.g., brain) at 37-50° C. for several days to clear the sample. The clearing process is faster at higher voltage and temperature, but requires more power, limiting the number of clearing setups simultaneously operable by one power supply (typical power output maximum, 300 W). For example, four setups can be run simultaneously at 37° C. and 30V, whereas only 2 setups can be run at 50° C. and 60V, so circulator temperature and voltage should be chosen to meet practical considerations.
2. After several days, wash the sample two times with PBST (0.1% TritonX in 1×PBS) twice for 24 hours each.

Preparing the Sample for Imaging:
1. Incubate the sample in FocusClear™ or 80% glycerol solution for 2 days before imaging. These solutions have refractive indices matching that of CLARITY-processed tissue. Ensure there is sufficient solution surrounding the sample, and that evaporative losses do not occur. Protect the sample from light.
2. Take a clean glass slide and gently place it on a dust-free surface.
3. Take a small piece of BluTack putty and prepare constant-diameter worm-shapes using gloved hands. Make the thickness uniform and about 1.5× the thickness of the sample (e.g. if the sample is 1 mm, make the putty tube diameter 1.5 mm).
4. Place two tubes of putty horizontally across the vertical slide, leaving space in between for the tissue sample. Cut excess putty that protrudes off the slide.
5. Using a spatula, carefully take the sample and place it between the putty tubes in the middle of the slide. Pipette ~20 μl of FocusClear™ medium on top of the sample.
6. Carefully place a Willco dish (with the lipped side facing up) on top of the putty tubes. Press down on the glass part of the dish (keeping fingers over the putty to avoid glass shattering) carefully and slowly until contact is made with the sample and FocusClear™ medium. Ensure that there are no bubbles between the sample, medium, slide, and dish.
7. Now using a P200 pipette, carefully introduce more FocusClear™ to either side of the sealed chamber (from the liquid that surrounded the sample for incubation as it has been optically matched). Take great care not to introduce any bubbles.
8. Now that the whole chamber is filled with FocusClear™, use PDMS sealant (Kwik-Sil) across both vertical openings between the putty, dish, and slide to fully seal the chamber and prevent evaporation.
9. Place aluminum foil on top of the chamber and place it on a level surface (shielded from light to minimize photodamage). Leave the sample for 10-15 minutes to allow the PDMS sealant to polymerize fully.
10. Preparation is now ready for imaging.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Process for Imaging Whole Tissue

A process was developed to image whole tissue (including whole organs/organisms) for precise three-dimensional (3-D) imaging, immunohistology, clinical diagnostics, and functionalization. By embedding a tissue in nano-porous hydrogel that physically supports the ultrastructure of the tissue and then electrophoretically removing only membrane lipids, the whole tissue becomes highly transparent and permeable to macro-molecules. This technology preserves proteins, small peptides, small molecules, and nucleic acids in the tissue in their three-dimensional distribution, secured by the fine hydrogel mesh. By bypassing destructive sectioning of the tissue, subcellular structures may be analyzed. In addition, tissue can be iteratively stained, unstained, and restained with other reagents for comprehensive analysis. An illustration of the process, termed "CLARITY," is provided in FIG. 1. Panel a: tissue is crosslinked using formaldehyde (red) in the presence of hydrogel monomers (blue). In this process, formaldehyde covalently links the monomers to biomolecules, such as proteins, nucleic acids, and small molecules. Panel b: next, biomolecule-bound monomers are polymerized into a hydrogel mesh. This hydrogel-tissue hybridization physically supports the structure of the tissue and chemically incorporates the biomolecules into the hydrogel mesh. Panel c: next, an electric field is applied across the hybrid immersed in an ionic detergent solution. Panel d: electrophoresis is used to actively transport ionic micelles into the hybrid and extract only membrane lipids out of the tissue, leaving structures and crosslinked biomolecules in place and available for imaging and molecular phenotyping. Panel e: whole tissue immunostaining can be conducted using antibodies. Detergent-mediated removal of the antibodies can be used to conduct multiple rounds of immunostaining on the same sample.

Example 2: Devices and Systems for CLARITY Process

An electrophoretic tissue clearing (ETC) chamber and associated components (including a temperature-controlled buffer circulator, buffer filter, and electrophoresis power supply) were developed to carry out portions of the CLARITY process described in Example 1. Illustrations of the devices and systems are provided in FIG. 2. Panel a: ETC setup consists of the custom ETC chamber, a temperature-controlled buffer circulator (RE415, Lauda, Germany), a buffer filter (Cat. No. 4422K61, McMaster, Robbinsville, N.J.), and a power supply (Cat. no. 164-5052, Biorad, Hercules, Calif.). The sample is electrophoresed by applying 20-60V to the electrodes. Buffer solution is circulated through the chamber to maintain temperature and the composition of the buffer solution constant throughout the clearing process. Panels b-d: ETC chamber design. Panel b shows various views of a representative device showing a cylindrical plastic housing, inlet/outlet ports (Cat. No. 5463K245, McMaster, Robbinsville, N.J.) and two platinum electrodes (Cat. No. 267201, Sigma, St. Louis, Mo.). The buffer inlet and outlet are located such that buffer flow through the chamber effectively removes air bubbles generated by electrolysis of the buffer solution. Panel c shows components of the assembly. Panel d shows a top cut-through view. The hydrogel-embedded tissue is placed in a sample holder (Cell Strainer, BD Biosciences, Durham, N.C.) located in the middle of the chamber between the two electrodes. The end of each electrode exposed outside the chamber is connected to a power supply. Examples of spatial dimensions of a chamber in accordance with embodiments of the invention are included in FIG. 8.

Example 3: Imaging of Intact Adult Mouse Brain Samples

Figure 3:
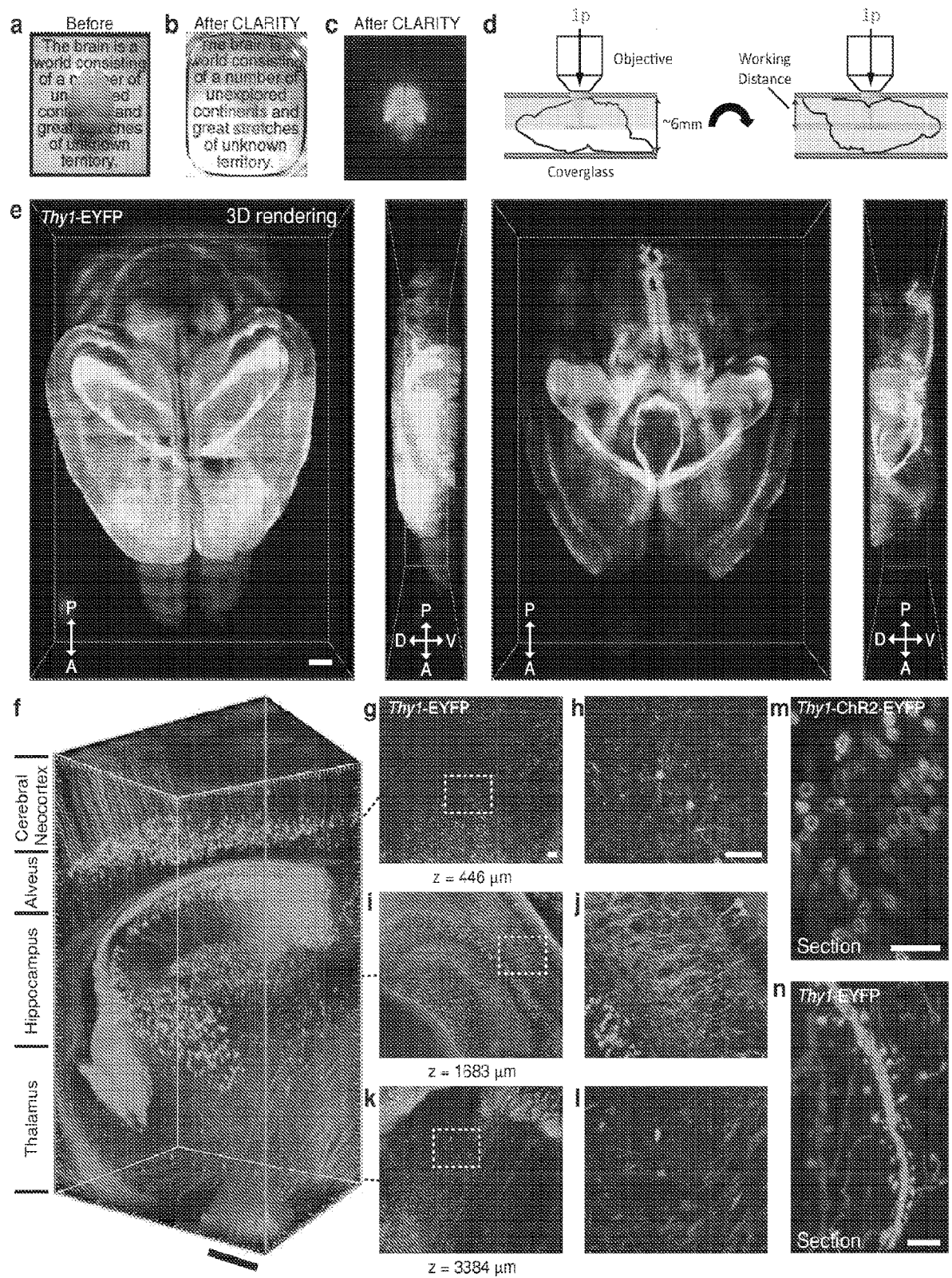
FIG. 3 is collection of images from intact adult mouse brain samples that were imaged using the CLARITY process.

Intact adult mouse brain samples were subjected to the CLARITY process and imaged. FIG. 3 shows the results. Panels a-d: images of whole mouse brains (three months old) with a Ramon y Cajal quote in the background. Panel a: before CLARITY. Panel b: after CLARITY: Thy1-EYFP H line brain after hydrogel-tissue hybridization, ETC, and refractive index (RI) matching with FocusClear™. Panel c: fluorescent image of the same brain shown in Panel b. Panel d: mounting of the whole cleared mouse brain for imaging. The brain is enclosed between two coverglasses. The dorsal half of the brain is first imaged using single photon (1P) excitation microscopy, and then the brain is inverted and the ventral half is imaged. Panel e: 3D reconstruction of the intact CLARITY-processed mouse brain (three months old) that was imaged using a 10× water immersion objective (numerical aperture (NA)=0.3, working distance=3.6 mm) and 514 nm excitation. Left, reconstruction of the dorsal half (dorsal to ventral, stack size=3100 µm, step size=20 µm). Right, reconstruction of the ventral half (ventral to dorsal, stack size=3400 µm, step size=20 µm). Scale bar, 1 mm. Panel f: 3D reconstruction of the non-sectioned mouse brain showing visualization through all layers of cortex, hippocampus, and thalamus (10× objective, stack size=3400 µm, step size=2 µm, 514 nm excitation). Scale bar, 400 µm. Panels g-l: three optical sections from Panel f at different depths showing negligible resolution loss even at the depth of ~3400 µm. Scale bar, 100 µm. Panel g: z=446 µm. Panel h: z=1683 µm. Panel i: z=3384 µm. Panels j-l: boxed regions in Panels g, h, and i, respectively. Panel m: image of a cross section of axon bundles in the striatum of Thy1-ChR2-EYFP line showing membrane-localized ChR2-EYFP after the CLARITY process. 1 mm-thick coronal block was CLARITY-processed and imaged using a 63× glycerol immersion objective (NA=1.3, working distance=280 µm). Scale bar, 5 µm. Panel n: high-resolution image showing well-preserved dendrites and dendritic spines of pyramidal neurons in the cortex of the CLARITY-processed Thy1-EYFP H line mouse. 1 mm-thick coronal block was imaged using the 63× glycerol objective. Scale bar, 5 µm.

Example 4: Molecular Phenotyping in Intact Tissue Volumes

Figure 4:
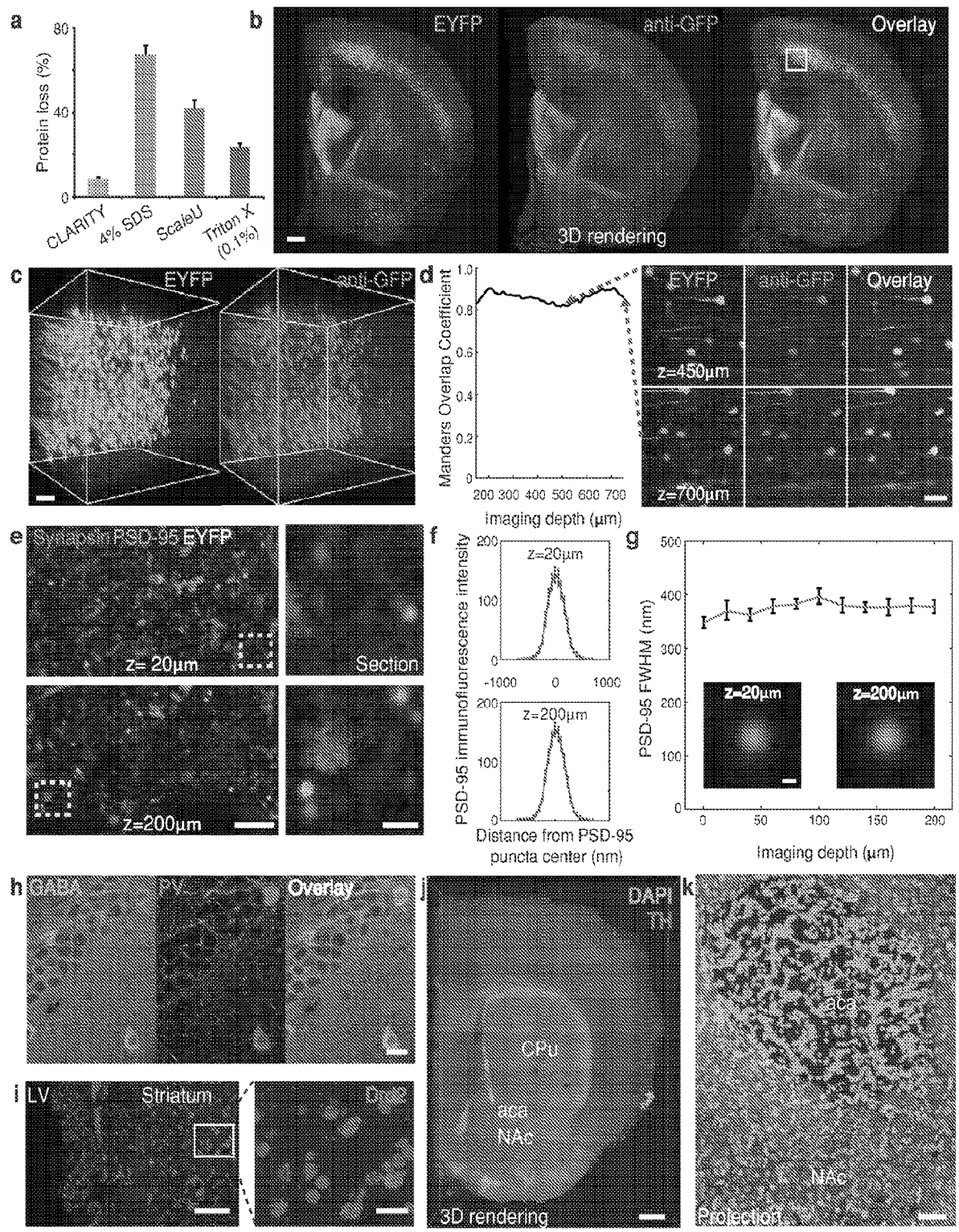
FIG. 4 is a collection of images and data showing molecular phenotyping results in intact tissue volumes processed using CLARITY.

Intact tissue volumes were processed using CLARITY and subjected to molecular phenotyping analysis. The results are shown in FIG. 4. Panel a: protein loss measurement (see Methods); error bars, s.e.m.; n=4 for each condition. Panel b: volume rendering of a 1 mm-thick coronal block of Thy1-EYFP mouse immunostained for GFP in intact non-sectioned form, showing uniform immunostaining. The intact block was ETC-cleared for one day and immunostained for three days (two days in GFP antibody conjugated with Alexa594 and one day wash) at 37° C. The block was then imaged using the 10× water-immersion objective and 1p excitation (514 nm and 591 nm). Left, EYFP (green). Middle, anti-GFP staining (red). Right, overlay. Scale bar, 500 µm. Panel c: enlarged 3D rendering of the boxed region in the cortex showing complete overlap of EYFP and anti-GFP staining. Panel d: co-localization analysis of the GFP staining. Manders Overlap Coefficient (MOC) was plotted as a function of tissue depth. Right, two optical sections at different depths from the 3D rendering on the left. Scale bar, 100 µm. Panels e-f: identification of individual synapses. A 500 µm-thick coronal block of H line mouse brain (two months old) was cleared for one day and immunostained for synapsin I (Red) and PSD-95 (green) for 3 days: primary (1 day)—wash (0.5 day)—secondary (1 day)—wash (0.5 day). The hippocampus was then imaged using the 63× glycerol objective and single photon (1P) excitation (514 nm, 591 nm, 651 nm). Panel e: left, two optical sections (z=20 µm and 200 µm). Right, enlarged images of the boxed regions. Individual synaptic puncta can be resolved throughout the depth. EYFP in white. Panel f: average immunofluorescence cross-section of PSD-95 puncta at z=20 µm (top) and z=200 µm (bottom). Error bars indicate 95% confidence interval of mean. Panel g: full width at half maximum (FWHM) of average immunofluorescence cross-section of PSD-95 puncta as a function of imaging depth. Nearly constant FWHM across depths suggests loss of resolution is negligible. Insets show average puncta at z=20 µm and 200 µm. Panels h-i: small molecules, proteins, and nucleic acids are well preserved, localized, and can be visualized using molecular probes in CLARITY-transformed tissue. Panel h: gamma-aminobutyric acid (GABA) and parvalbumin (PV) staining in the hippocampus showing co-localization of GABA and PV. Left, GABA. Middle, PV. Right, overlay. A 500 µm-thick coronal block of wild-type mouse brain (three months old) was cleared for one day and immunostained for 3 days: primary (1 day)—wash (0.5 day)—secondary (1 day)—wash (0.5 day). The block was then imaged using a 25× water-immersion objective (NA=0.95, working distance=2.5 mm) and single photon excitation (488 nm and 591 nm). Scale bar, 20 µm. Panel i: in situ hybridization (ISH) on CLARITY-transformed mouse brain block showing dopamine receptor D2 (drd2) mRNA localization around the cell body in the striatum (AP: −1.7; DV: −2.3; ML: 2.6). LV, lateral ventricle. Blue, DAPI. 50 bp RNA probes for drd2 were hybridized with a 500 µm-thick CLARITY-processed coronal block and visualized with FastRed. The block was imaged using the 25× water-immersion objective, single photon excitation (555 nm) for FastRed, and two photon excitation for DAPI (720 nm). Scale bar: left, 100 µm; right, 20 µm. Panels j-k: axonal fibers of TH-positive neurons in the nucleus accumbens (NAc) and caudate-putamen (CPu) of mouse brain. Panel j: 3D rendering of 1 mm-thick mouse brain block (Bregma 1.10→0.10) stained for TH (red) and DAPI (green). aca, anterior commissure; scale bar 500 µm. Panel k: maximum projection of 50 µm volume of the NAc and aca in Panel j. Scale bar, 50 µm.

Example 5: Multi-Round Molecular Phenotyping of Intact Tissue

Figure 5:
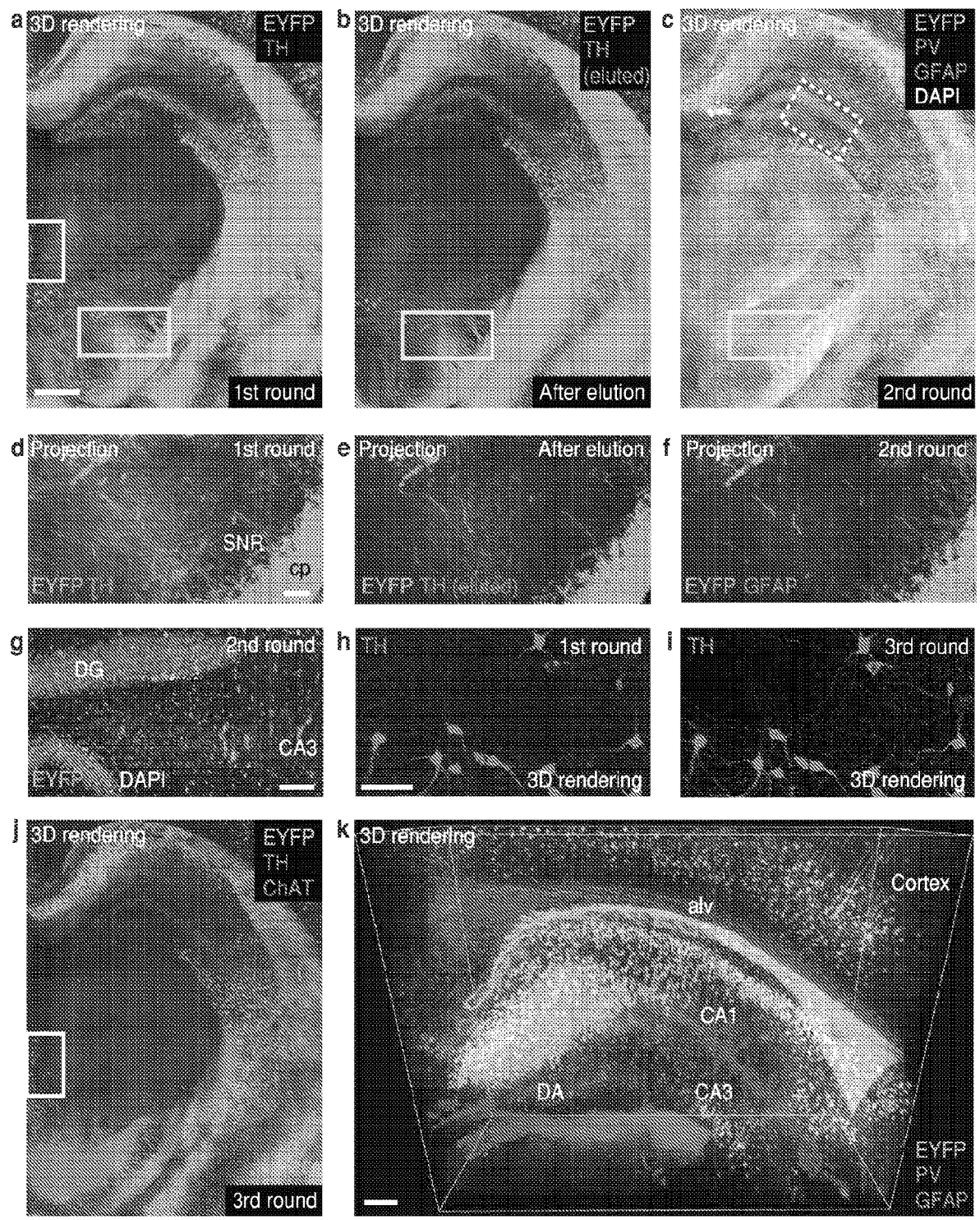
FIG. 5 is a collection of images showing multi-round molecular phenotyping of intact tissue using CLARITY.

Intact tissue samples were processed using CLARITY and subjected to multi-round molecular phenotyping analysis. Results are shown in FIG. 5. Panel a: 1st round staining. Volume rendering of a 1 mm-thick coronal block (bregma −2.5 mm) of Thy1-EYFP mouse immunostained for tyrosine hydroxylase (TH) in intact non-sectioned form. The block was ETC-cleared for 1 day and immunostained for six days: primary (2 day)—wash (1 day)—secondary (2 day)—wash (1 day). Scale bar, 500 µm. Panel b: antibody elution. The imaged antibodies were eluted from the block shown in Panel a by incubating the block in 4% SDS solution at 60° C. for 0.5 days. Note that the TH signal was completely removed while the fluorescence signal of EYFP was retained. Panel c: 2nd round staining. 3D rendering of the same block immunostained for PV (red) and GFAP (blue). DAPI (white) was used to counterstain nuclei. Panels d-f: maximum projections of 100 µm-volume of yellow-boxed region in Panels a, b, and c, respectively. Note that patterns of EYFP-positive neurons, as well as cellular morphologies, are very similar; tissue architecture and cellular structures are well preserved throughout the process of multi-round staining. SNR, substantia nigra; cp, cerebral peduncle; scale bar, 100 µm. Panel g: optical section of white-/dotted-boxed region in Panel c showing strong DAPI signal. DG, dentate gyrus; scale bar, 100 µm. Panels h-i: TH channel of white-boxed region in Panel a (Panel h) and Panel j (Panel i). The pattern and signal intensity of TH staining is similar between the 1st round and 3rd round; antigens and antigenicity are well preserved after two sequential antibody elution processes. Scale bar, 100 µm. Panel j: $3^{rd}$ round staining. The same block shown in Panels a-c was immunostained for TH (red) and ChAT (blue). Panel k: enlarged 3D view of the hippocampus in Panel c showing distribution of EYFP-expressing neurons (green), PV-positive neurons (red), and GFAP (blue). Alv, alveus of hippocampus; scale bar, 200 µm.

Example 6: Structural Mapping and Molecular Phenotyping of Human Brain Samples

Figure 6:
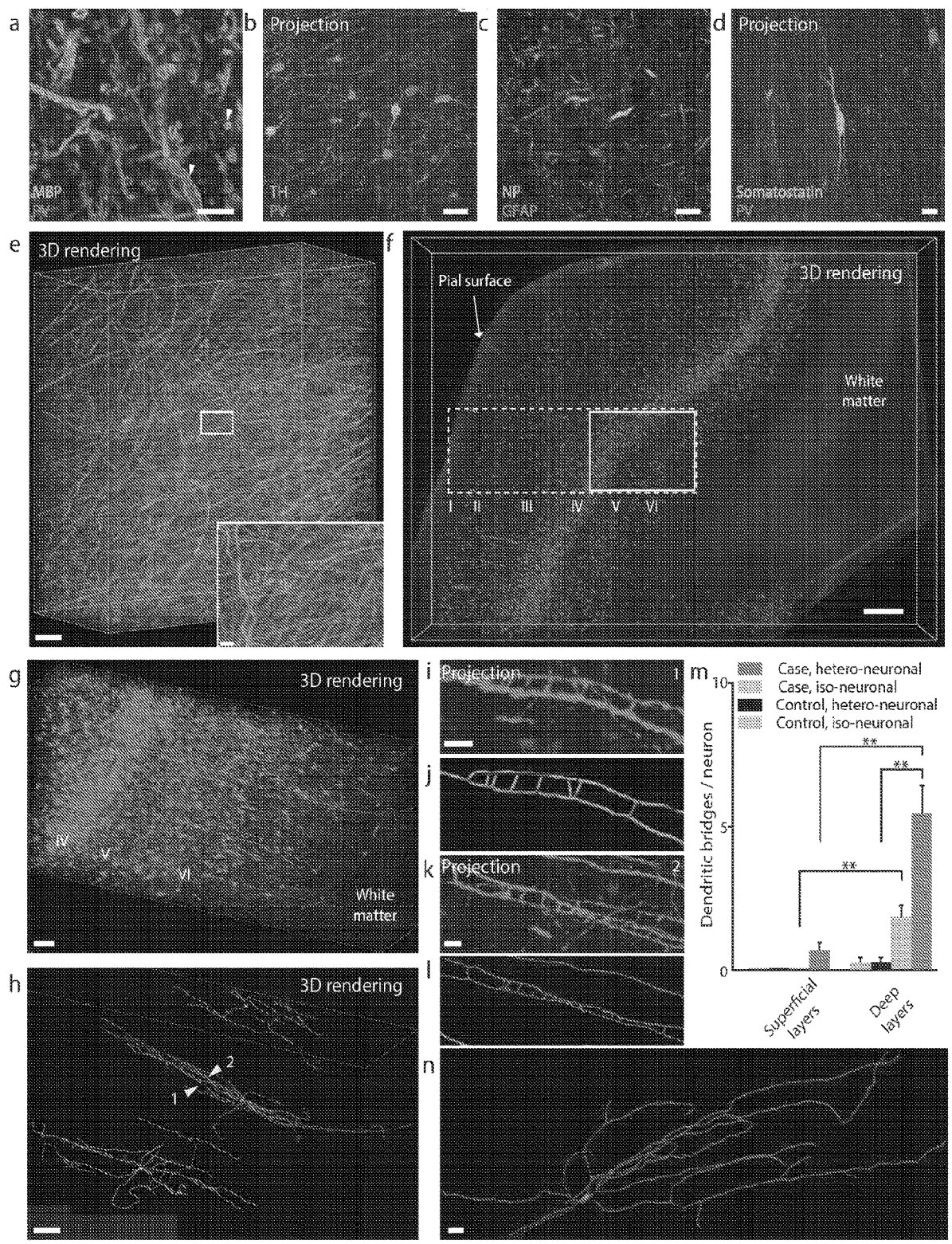
FIG. 6 is a collection of images and data showing results of human brain structural mapping and molecular phenotyping using CLARITY.

Human brain samples were processed using CLARITY and subjected to structural mapping and molecular phenotyping analysis. Results are shown in FIG. 6. Panels a-g, i, k: immunostaining of CLARITY-processed frontal lobe (BA 10) of postmortem human brain (Autism Tissue Program case #AN13961; age, 7 years; sex, male; PMI, 25; storage, 82 months in 10% formalin at room temperature). 500 µm-thick intact blocks were cleared for 1 day and immunostained for 3 days as follows: primary (1 day)—wash (0.5 day)—secondary (1 day)—wash (0.5 day). Stained blocks were imaged using the 25× water immersion objective. Panel a: optical section showing myelin basic protein (MBP) and PV staining. White arrowheads indicate membrane-localized MBP wrapping around PV-positive projections. Scale bar, 10 µm. Panel b: TH and PV staining. Maximum projection of a 120 µm-thick volume image. Step size, 0.5 µm; scale bar, 50 µm. Panel c: optical section showing Neurofilament (NP) and GFAP staining. Scale bar, 20 µm. Panel d: somatostatin and PV staining. Maximum projection of a 63 µm-thick volume image. Step size, 0.5 µm; scale bar, 20 µm. Panel e: 3D reconstruction of NP-positive axonal fibers. Red, traced axon running across the volume. Scale bar, 500 µm; Inset, enlarged image of the boxed region (scale bar, 20 µm). Panel f: visualization of PV-positive neurons in the neocortex of the autism case. A 500 µm-thick intact block was cleared and stained as described above, and subcortical layers were identified. Scale bar, 500 µm. Panel g: yellow-boxed region in Panel f showing PV-positive neuronal cell bodies and fibers in layers IV, V, and VI. Three representative PV-positive interneurons in layer VI with ladder-shaped hetero- or iso-neuronal connections were traced (green, purple, blue). Scale bar, 100 µm. Panel h: 3D reconstruction of the three abnormal neurons in Panel g. Scale bar, 80 µm. Panel i: zoomed-in maximum projection of 8 µm volume image showing morphological details of the ladder-shaped structure formed by neurites from a single neuron. Scale bar, 10 µm. Panel j: tracing of the structure shown in Panel i. Panel k: maximum projection of 18 µm volume image showing a ladder-shaped structure formed by neurites from two different neurons. Scale bar, 10 µm. Panel l: tracing of the structure shown in Panel k. Panel m: bar graph showing iso- or hetero-neuronal dendritic bridges per neuron. Neurons were selected randomly and traced in software (see Methods); dendritic bridges were manually counted. **$P<0.05$; error bars, s.e.m.; n=6 for both superficial and deep layers of the autism case. n=4 for both superficial and deep layers of the control case (#AN10251; age 10 years; sex, male; PMI, 19.83). Panel n: 3D reconstruction of a neuron in layer II (superficial) of the autism case; typical avoidance of iso-dendritic contact was observed.

Example 7: Preservation of GFP and TdTomato Signals

Figure 7:
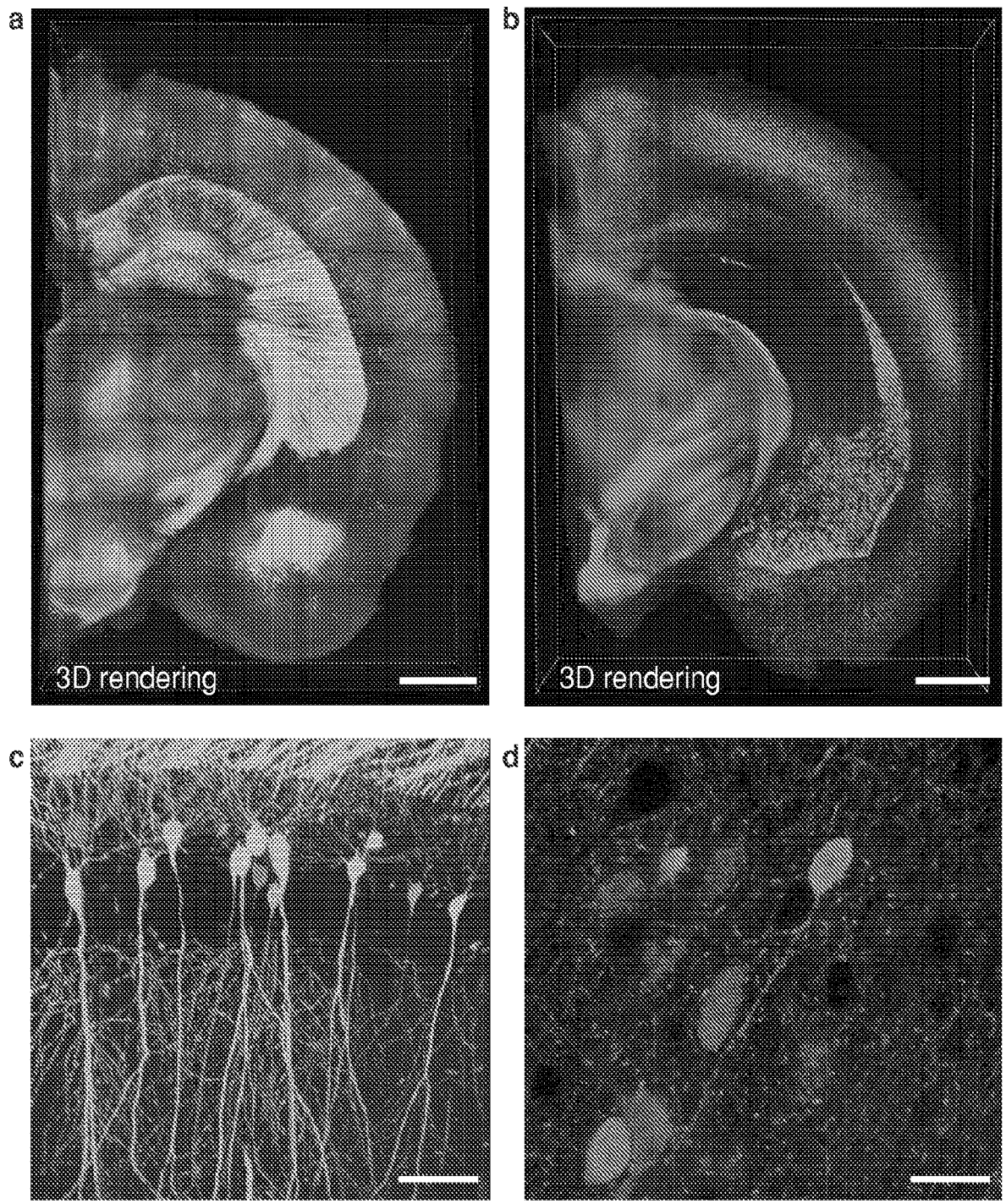
FIG. 7 is a collection of images showing results from mouse brain tissue that was imaged using CLARITY.

Transgenic mouse brain samples were processed using CLARITY and subjected to imaging analysis. The results are shown in FIG. 7. Panel a: 3D rendering of a 1 mm-thick Thy1-EGFP M line mouse brain block processed by CLARITY (Bregma $-1.6 \rightarrow -2.6$) showing distribution of EGFP-expressing neurons and projections. Scale bar, 1 mm. Panel b: 3D rendering of a 1 mm-thick mouse coronal block of PV-Cre mouse line (B6; 129P2-Pvalb$^{tm1(cre)Arbr}$/J) crossed with TdTomato reporter line (B6;129S6-Gt(ROSA) 26Sor$^{tm9(CAG-tdTomato)Hze}$/J) Scale bar, 1 mm. Panel c: maximum projection of 300 µm volume of the hippocampus in Panel a showing EGFP-expressing neurons and their neurites. Scale bar, 50 µm. Panel d: high resolution optical section from the tissue in Panel b showing TdTomato-expressing neurons in the cortex. Scale bar, 25 µm. The results demonstrate that GFP and TdTomato signals are preserved during the CLARITY process.

Example 8: Electrophoretic Tissue Clearing (ETC) Device

An ETC device was designed and constructed to carry out the CLARITY process. An example of an ETC device in accordance with embodiments of the invention is shown in FIG. 8. Panels a-d: various views of a representative device showing a cylindrical plastic housing, inlet/outlet ports (Cat. No. 5463K245, McMaster, Robbinsville, N.J.) and two platinum electrodes (Cat. No. 267201, Sigma, St. Louis, Mo.). The buffer inlet and outlet are located such that buffer flow through the chamber effectively removes air bubbles generated by electrolysis of the buffer solution. Panels e-h: components of the assembly and example dimensions of a representative device. All dimensions are in millimeters. Panels i-j: sections through the device in Panel i (isometric) and Panel j (top view) indicate component positions in the assembled chamber. The hydrogel-embedded tissue is placed in the sample holder (Cell Strainer, BD Biosciences, Durham, N.C.) located in the middle of the chamber between the two electrodes. The single end of each electrode that is exposed outside the chamber is connected to a power supply.

Example 9: Optical Tissue Clearing of Intact Adult Mouse Brain Using FocusClear™ and Glycerol Intact adult mouse brain samples were processed using CLARITY and FocusClear™ and glycerol solutions. The results are shown in FIG. 9. Panel a: an image of a PFA-fixed/hydrogel-embedded/non-ETC cleared mouse brain (four weeks old) incubated in FocusClear™ for two days at room temperature. Panel b: the same mouse brain shown in Panel a incubated in FocusClear™ for eight days at room temperature. Panel c: an image of a PFA-fixed/hydrogel-embedded/non-ETC cleared mouse brain (four weeks old) incubated in 85% glycerol for four days at 37° C. Panel d: an image of PFA-fixed/hydrogel-embedded/ETC cleared mouse brain (four weeks old) incubated in 85% glycerol for two days at room temperature.

Example 10: Electron Microscope (EM) Imaging of CLARITY-Processed Samples

Figure 10:
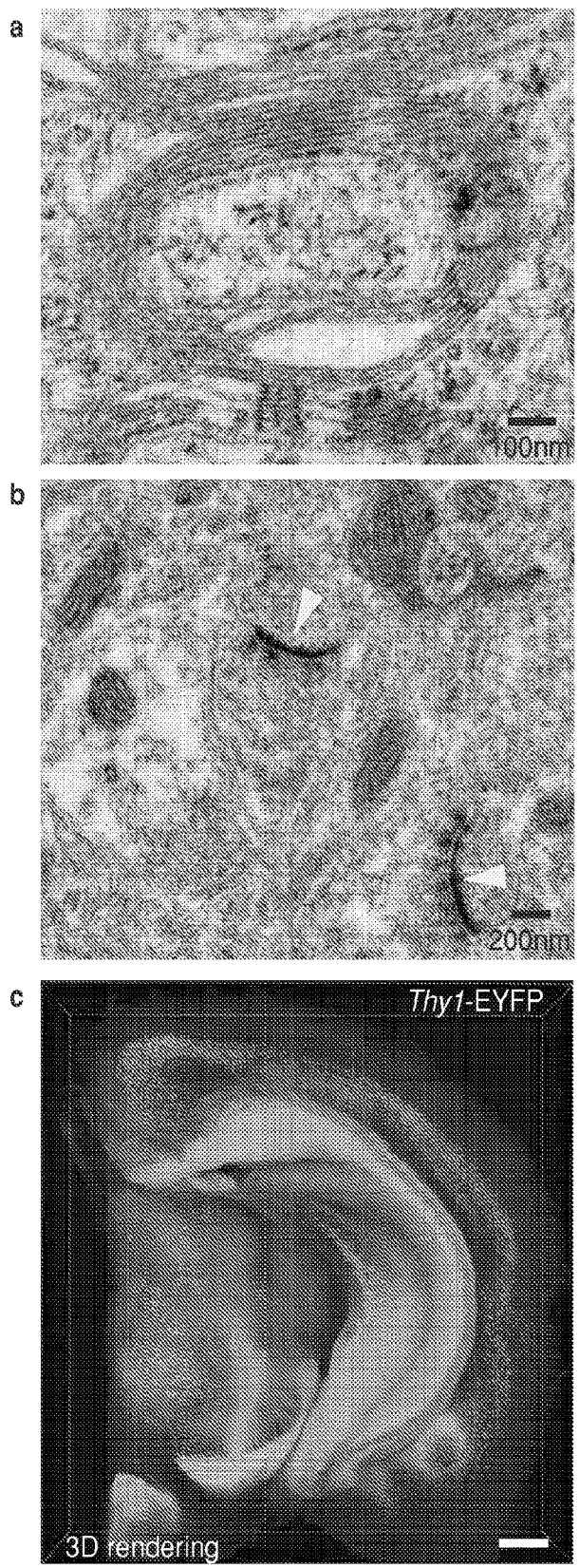
FIG. 10 is a collection of images showing results from electron microscope (EM) imaging of CLARITY-processed mouse brain tissue. The images demonstrate EM-compatibility of the CLARITY process.

Mouse brain tissue samples were processed using CLARITY and then imaged using electron microscopy. The results are shown in FIG. 10, and demonstrate EM-compatibility of the CLARITY process. A Thy1-EYFP H line mouse (4 months old) was perfused transcardially with a mixture of 2 wt % paraformaldehyde/2 wt % glutaraldehyde/4% acrylamide (wt/vol)/0.05% bis-acrylamide (wt/vol)/0.25% VA044 (wt/vol)/PBS. Hydrogel-embedded brains were ETC-cleared for four days. Cleared tissue was imaged using the 10× water-immersion objective (3D rendering shown in Panel c). After imaging, the tissue was post-fixed in 1% Osmium tetroxide (EMS Cat#19100) for 1 hr at RT, washed 3× with ultra-filtered water, and then en-bloc stained for 2 hrs at RT. Samples were then dehydrated in a series of ethanol washes for 15 minutes each at 4° C. (50%→70%→95% (whereupon samples were allowed to warm to RT)→100% (2×)→acetonitrile for 15 min). Samples were infiltrated with EMbed-812 resin (EMS Cat#14120) mixed 1:1 with acetonitrile for 2 hrs followed by a 2:1 mixture of EMbed-812:acetonitrile for 2 hours. Samples were then placed into EMbed-812 for 2 hours, followed by TAAB capsules filled with fresh resin, then placed into 65° C. oven overnight. Sections were cut between 75 and 90 nm on a Leica Ultracut S (Leica, Wetzlar, Germany), and picked up on formvar/carbon coated slot grids (EMS Cat# FCF2010-Cu) or 100 mesh Cu grids (EMS Cat#FCF100-Cu). Grids were contrast-stained for 30 seconds in 3.5% UrAcetate/50% acetone followed by staining in 0.2% lead citrate for 30 seconds. Observation was in the JEOL JEM-1400 TEM at 120 kV and photos were taken using a Gatan Orius digital camera. Panel a: TEM image showing myelinated axons in the hippocampus. Scale bar, 100 nm. Panel b: TEM image showing post-synaptic densities (yellow arrowheads) in the hippocampus. Scale bar, 200 nm. Panel c: 3D rendering of a cleared 1 mm-thick Thy1-EYFP H line mouse block before EM sample preparation. Mouse brain tissues fixed using 2% glutaraldehyde for EM were cleared and imaged using CLARITY.

Example 11: Molecular Phenotyping of Whole Mouse Brain Samples

Figure 11:
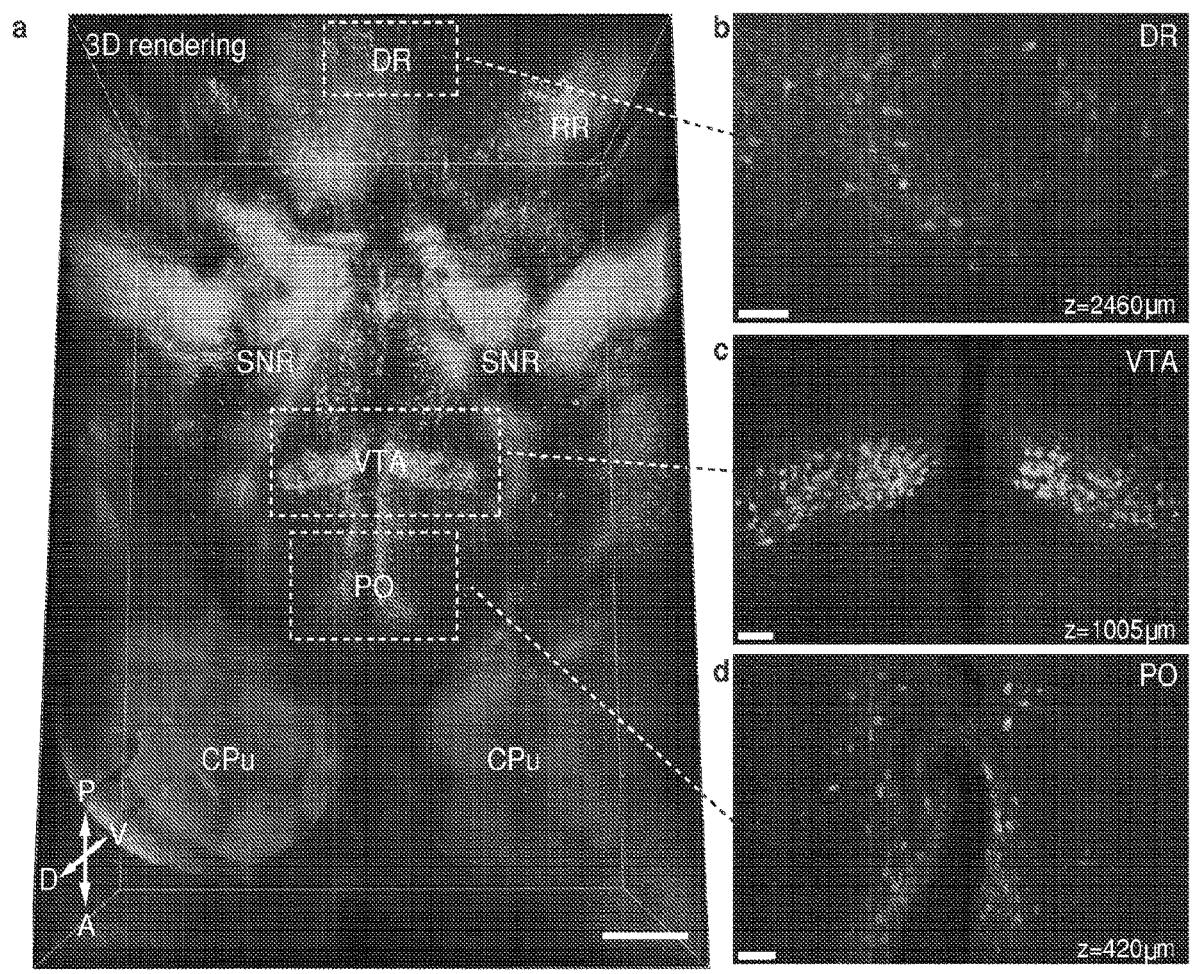
FIG. 11 is a collection of images showing results from whole mouse brain molecular phenotyping.

Whole mouse brain samples were processed using CLARITY and subjected to molecular phenotyping analysis. The results are shown in FIG. 11. Panel a: 3D immunohistological visualization of the TH-positive neurons and their fibers in the intact mouse brain. The intact brain was ETC-cleared for three days and stained for six weeks: primary (2 weeks)—wash (1 week)—secondary (2 weeks)—wash (1 week), and imaged at 2500 µm from ventral side using the 10× water immersion objective. Scale bar, 700 µm. Panels b-d: optical sections at different depths. Note that TH-positive neurons are well labeled and clearly visible even at 2500 μm-deep in the intact brain. CPu, caudate putamen; PO, preoptic nucleus; VTA, ventral tegmental area; SNR, substantia nigra; RR, retrorubral nucleus; DR, dorsal raphe; Scale bar, 100 μm.

Figure 12:
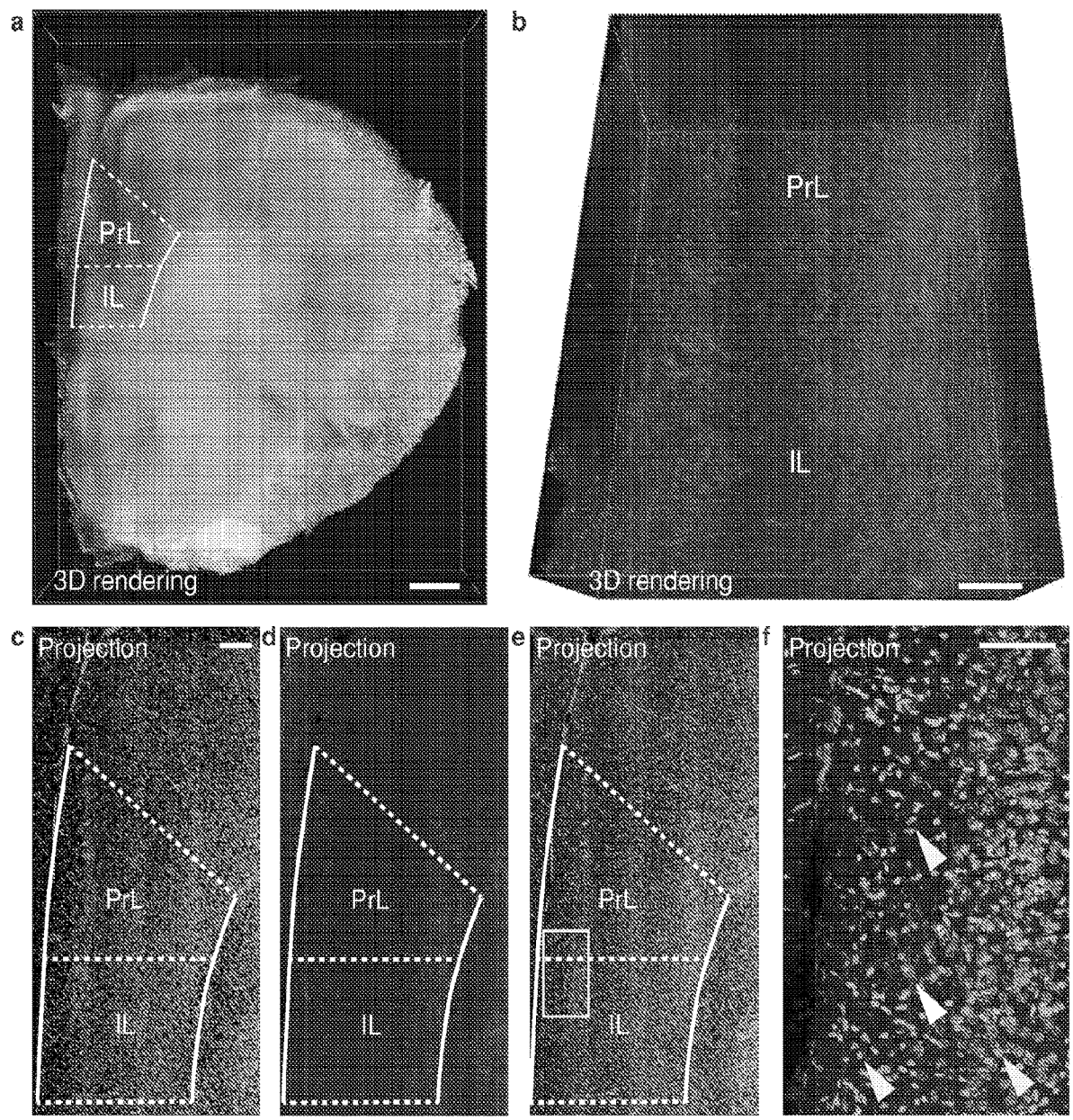
FIG. 12 is a collection of images showing axonal fibers of the TH-positive neurons in the prefrontal cortex of a mouse brain imaged using the CLARITY process.

Example 12: Imaging of Axonal Fibers in the Prefrontal Cortex of Mouse Brain Samples Mouse brain samples were processed using CLARITY and the axonal fibers of the TH-positive neurons in the prefrontal cortex were imaged. Results are shown in FIG. 12. Panel a: 3D rendering of 1 mm-thick mouse brain block (Bregma 2.68→1.68) stained for TH (red) and DAPI (green). The block was ETC-cleared for 1 day and immunostained for six days: primary (2 day)—wash (1 day)—secondary (2 day)—wash (1 day). PrL, prelimbic cortex; IL, infralimbic cortex; Scale bar, 500 μm. Panel b: zoom-in 3D rendering showing TH fibers in the IL/PrL. Scale bar, 200 μm. Panels c-e: maximum projection of 50 μm-volume of the IL/PrL in Panel a. Scale bar, 200 μm. Panel c: DAPI; Panel d: TH; Panel e: DAPI and TH; Panel f: yellow-boxed region in Panel e showing a heavily invested cell (white arrowhead) and non-innervated cells (yellow arrowheads). Scale bar, 100 μm.

Figure 13:
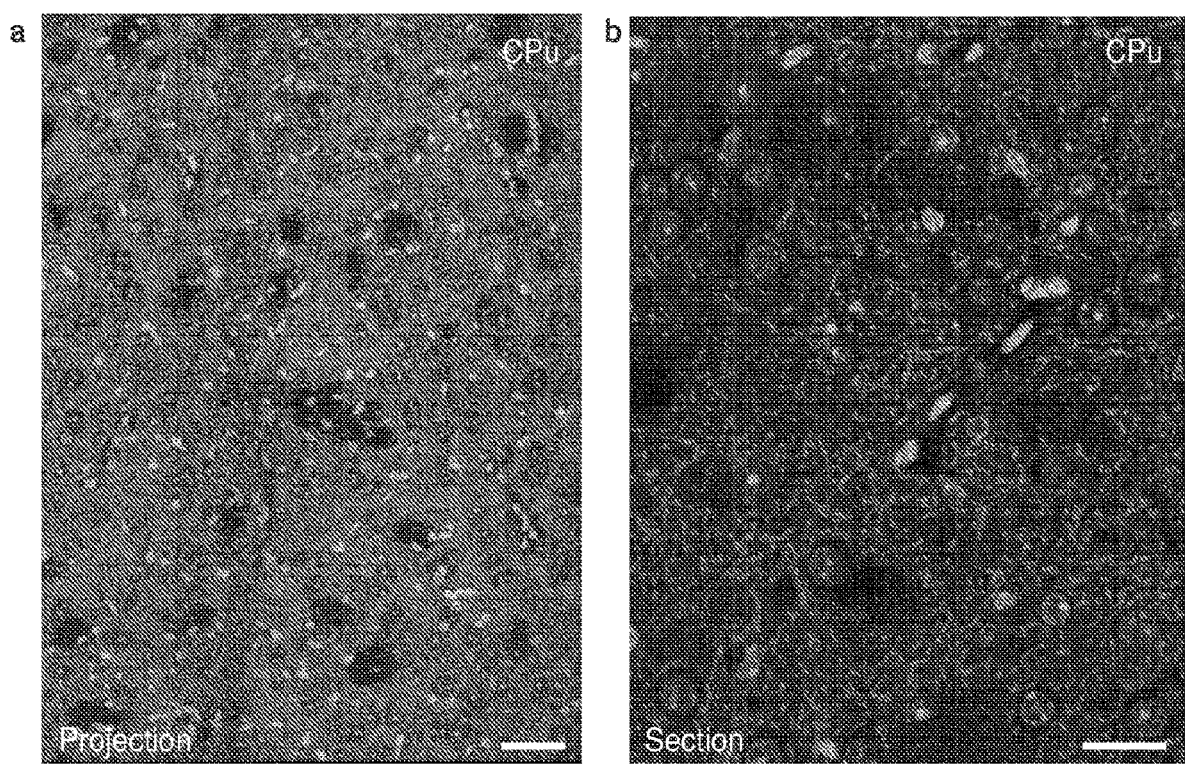
FIG. 13 is a collection of images showing axonal fibers of the TH-positive neurons in the nucleus accumbens and striatum of a mouse brain imaged using the CLARITY process.

Example 13: Imaging of Axonal Fibers in the Nucleus Accumbens and Striatum of Mouse Brain Samples Mouse brain samples were processed using CLARITY and the axonal fibers of the TH-positive neurons in the nucleus accumbens and striatum were imaged. Results are shown in FIG. 13. Panel a: maximum projection of 20 μm-volume of the CPu in FIG. 4, Panel j. The 1 mm-thick mouse brain block (Bregma 1.10→0.10) was ETC-cleared for 1 day and immune-stained for six days: primary (2 day)—wash (1 day)—secondary (2 day)—wash (1 day). CPu, caudate putamen; aca, anterior commissure; NAc, nucleus accumbens; Scale bar, 50 μm. TH (red) and DAPI (green). Panel b: optical section of the CPu in Panel a showing cells massively invested by TH fibers. Scale bar, 50 μm.

Example 14: Imaging of Axonal Fibers in the Amygdala of Mouse Brain Samples

Figure 14:
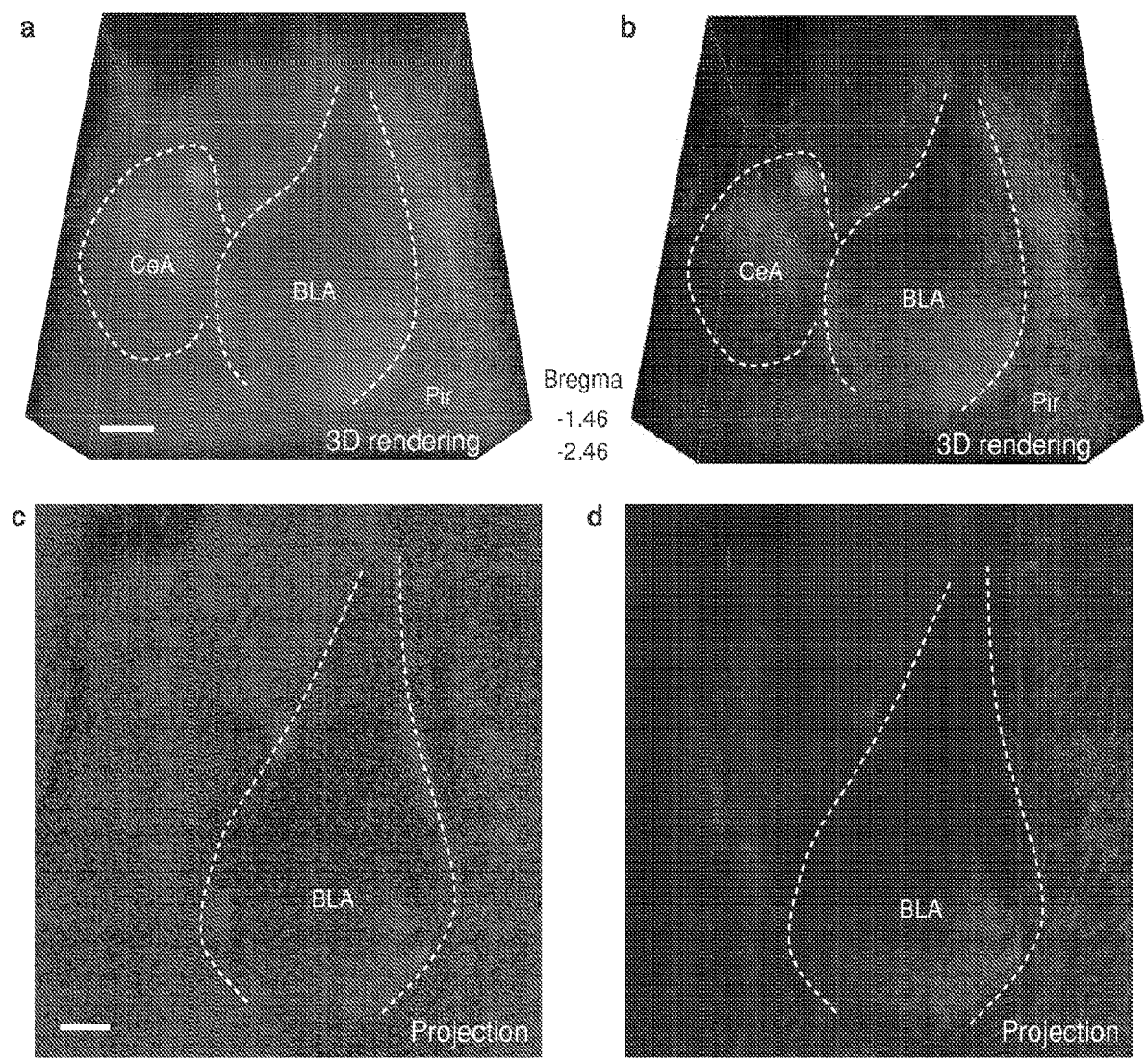
FIG. 14 is a collection of images showing axonal fibers of the TH-positive neurons in amygdala of mouse brain imaged using the CLARITY process.

Mouse brain samples were processed using CLARITY and the axonal fibers of the TH-positive neurons in the amygdala were imaged. Results are shown in FIG. 14. Panels a-d: a 1 mm-thick mouse brain block (Bregma −1.46→−2.46) was ETC-cleared for 1 day and immune-stained for six days: primary (2 day)—wash (1 day)—secondary (2 day)—wash (1 day). Panels a-b: 3D rendering of the tissue stained for TH (red) and DAPI (blue). BLA, basolateral amygdaloid nucleus; CeA, central amygdale; Pir, piriform cortex; Scale bar, 300 μm. Panel b: TH only. Panels c-d: maximum projection of 100 μm-volume in Panel a. Scale bar, 200 μm. Panel d: TH only.

Figure 15:
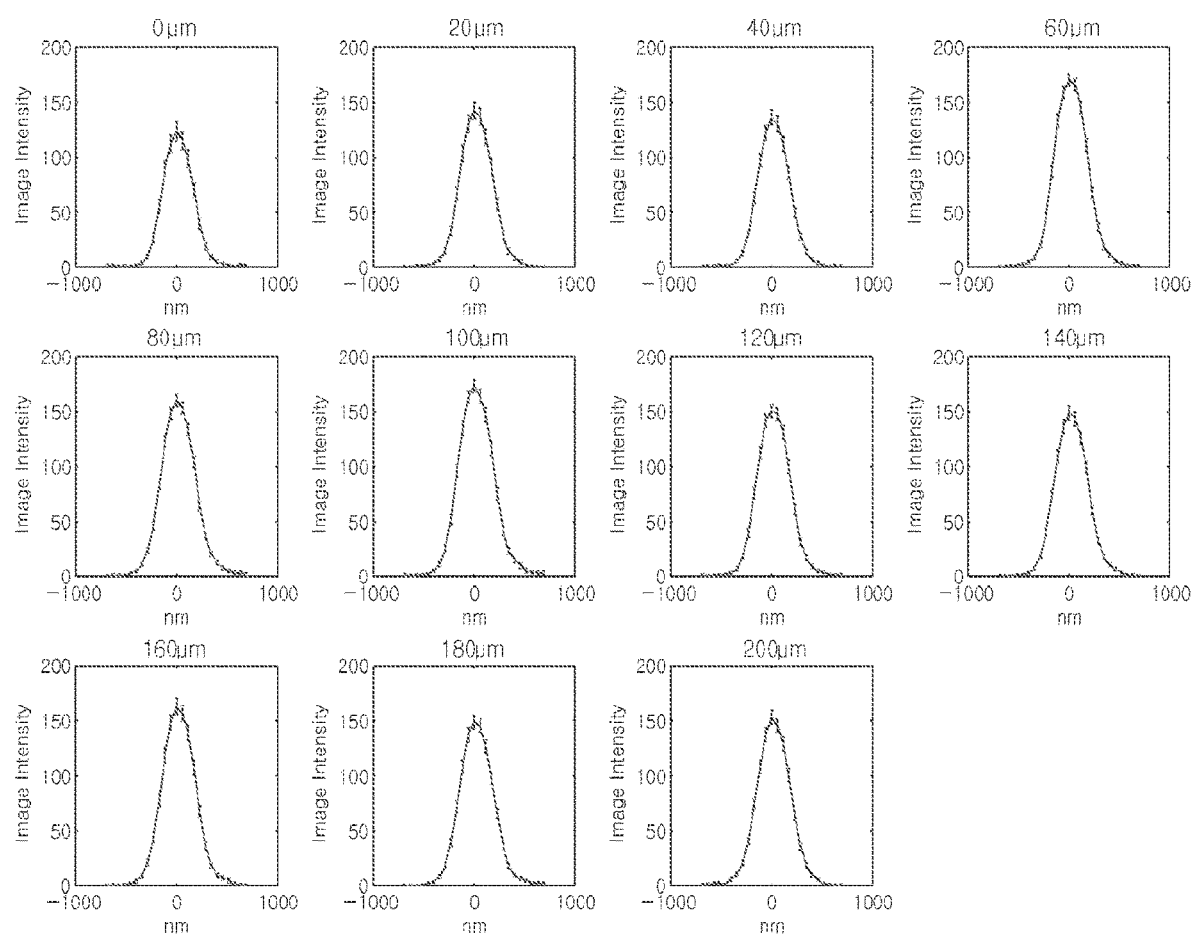
FIG. 15 is a series of graphs showing the average immunofluorescence cross-section of PSD-95 puncta at different depths (0-200 μm, 20 μm interval).

Example 15: Measurement of Average Immunofluorescence Cross-Section of PSD-95 Puncta at Varying Depths in Tissue Volumes Processed Using CLARITY Intact tissue volumes were processed using CLARITY and the average immunofluorescence cross-section of post-synaptic density (PSD)-95 puncta was measured at different depths (0-200 μm, 20 μm interval). The results are shown in FIG. 15. The average fluorescence intensity of PSD-95 puncta was estimated at each depth by applying a circular Hough transform to the gradient field of the PSD-95 images (custom Matlab software). This located the center of all puncta with radii ranging from 114 nm to 684 nm (N between 31 and 108). The centers were aligned to compute the average puncta at each depth and the cross-section and the full width at half maximum was calculated (see graph shown in FIG. 4, Panel g).

Figure 16:
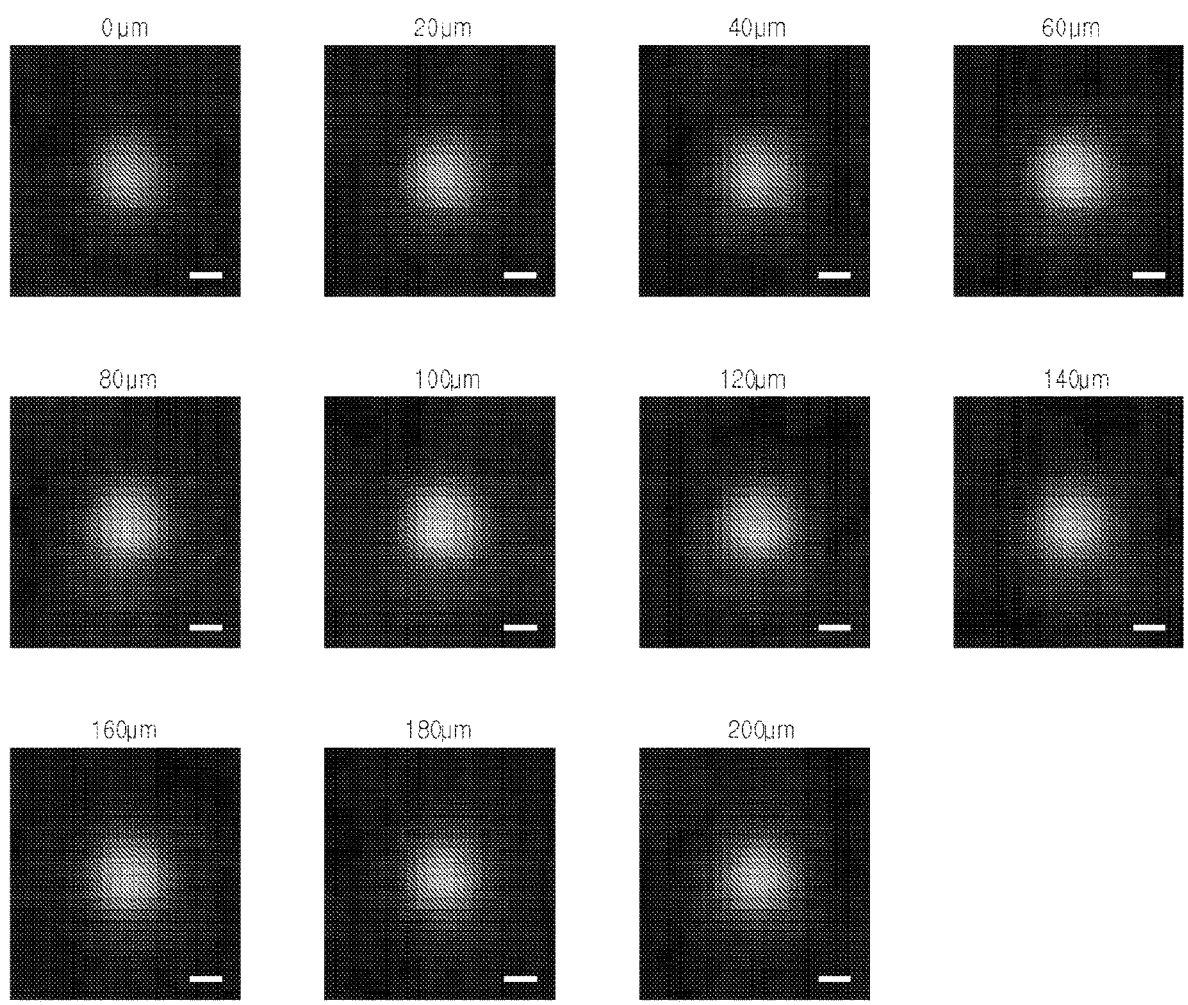
FIG. 16 is a series of images showing the average PSD-95 puncta at different depths (0-200 μm, 20 μm interval).

Example 16: Measurement of Average PSD-95 Puncta at Varying Depths in Tissue Volumes Processed Using CLARITY Intact tissue volumes were processed using CLARITY and the average post-synaptic density (PSD)-95 puncta was measured at different depths (0-200 μm, 20 μm interval). The results are shown in FIG. 16. Scale bar, 200 μm. The method described in Example 14 was used.

Figure 17:
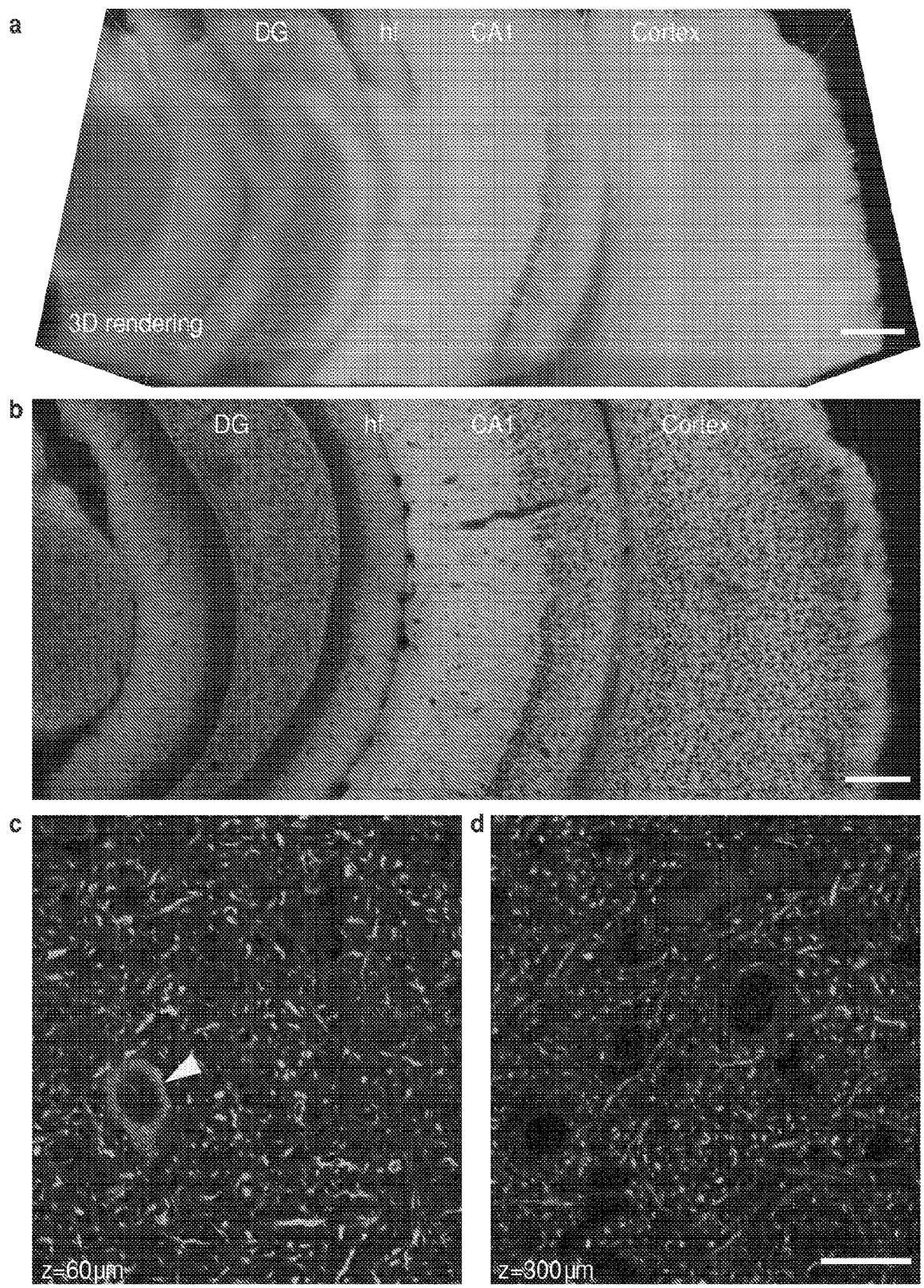
FIG. 17 is a collection of images showing microtubule-associated protein 2 (MAP2) staining showing uniform labeling of dense dendritic fibers and neuronal cell bodies throughout a 1 mm-thick mouse brain tissue sample imaged using the CLARITY process.

Example 17: MAP2 Staining of Dendritic Fibers and Neuronal Cell Bodies in Mouse Brain Tissue Mouse brain tissue samples were processed using CLARITY and were stained for microtubule-associated protein 2 (MAP2). The results are shown in FIG. 17, and demonstrate uniform labeling of dense dendritic fibers and neuronal cell bodies throughout the 1 mm-thick mouse brain tissue. Panel a: 3D rendering of 1 mm-thick mouse brain tissue stained for MAP2, which is expressed in neuronal cell bodies and their dendritic projections. The block was ETC-cleared for 1 day and immune-stained for six days: primary (2 day)—wash (1 day)—secondary (2 day)—wash (1 day). hf, hippocampal fissure; DG, dentate gyrus; scale bar, 300 μm. Panel b: an optical section from the 3D rendering. Scale bar, 250 μm. Panels c-d: high resolution optical sections at two different depths in the DG showing cross sections of the labeled fibers. Note that individual cross-sections of the dendritic fibers and weakly-labeled neuronal cell bodies (yellow arrowhead) can be clearly identified throughout the imaging depth. The images were taken using the 63× glycerol-immersion objective. Scale bar, 25 μm.

Example 18: Molecular Imaging of Whole Adult Zebrafish Brain

Figure 18:
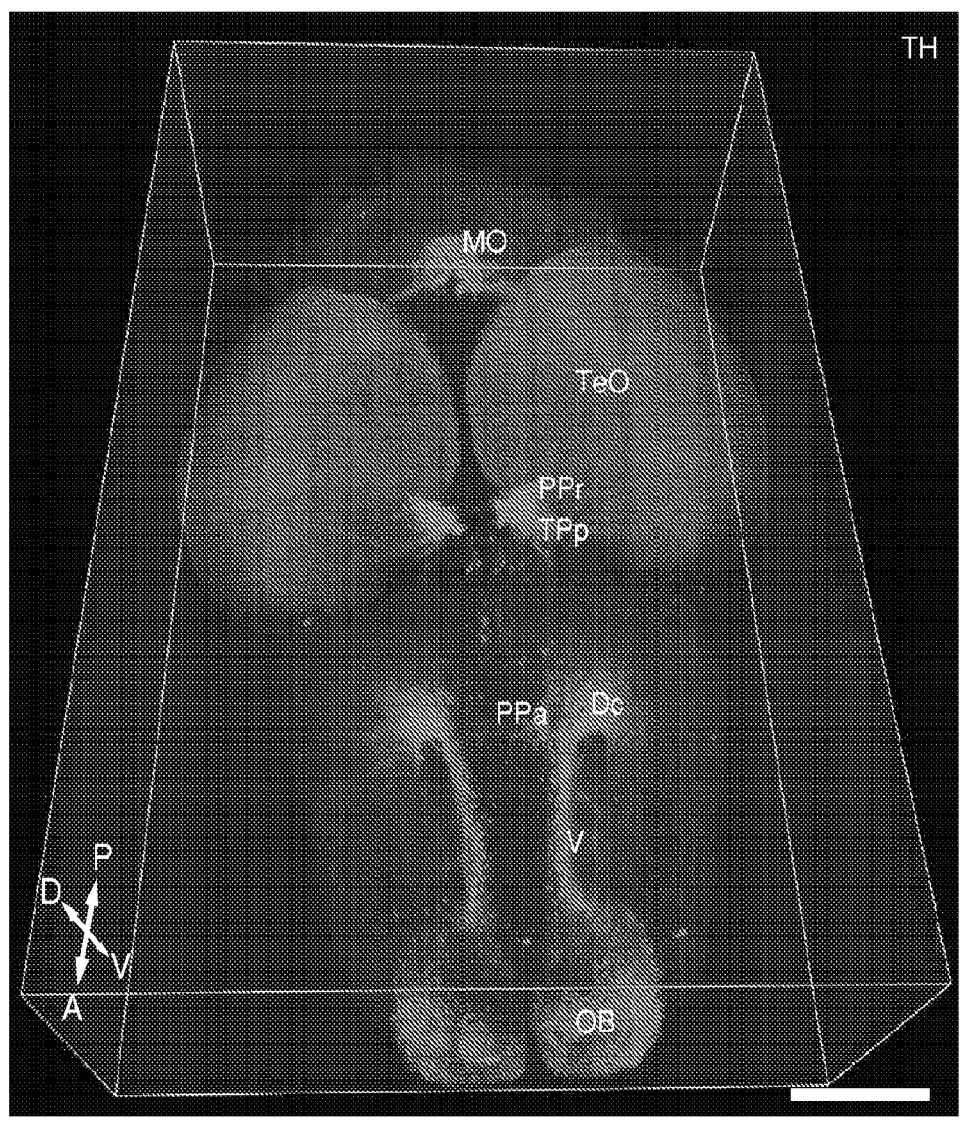
FIG. 18 is an image showing results from whole adult zebrafish brain molecular phenotyping.

A whole adult zebrafish brain was processed using CLARITY and subject to molecular phenotyping analysis. The results are shown in FIG. 18. Adult zebrafish brain was extracted from a 213 dpf (days post fertilization) fish, hydrogel-hybridized, and cleared by incubating in 4% SDS solution for 15 days. The cleared brain was stained with anti-tyrosine hydroxylase (TH) primary for four days and Alexa fluor 594 secondary for three days. The brain was then imaged with the 25× water immersion objective. 3D volume data (3,406×2,589×1,108 μm; step-size=5 μm). Red, TH; Blue, autofluorescence; scale bar, 100 μm.

Figure 19:
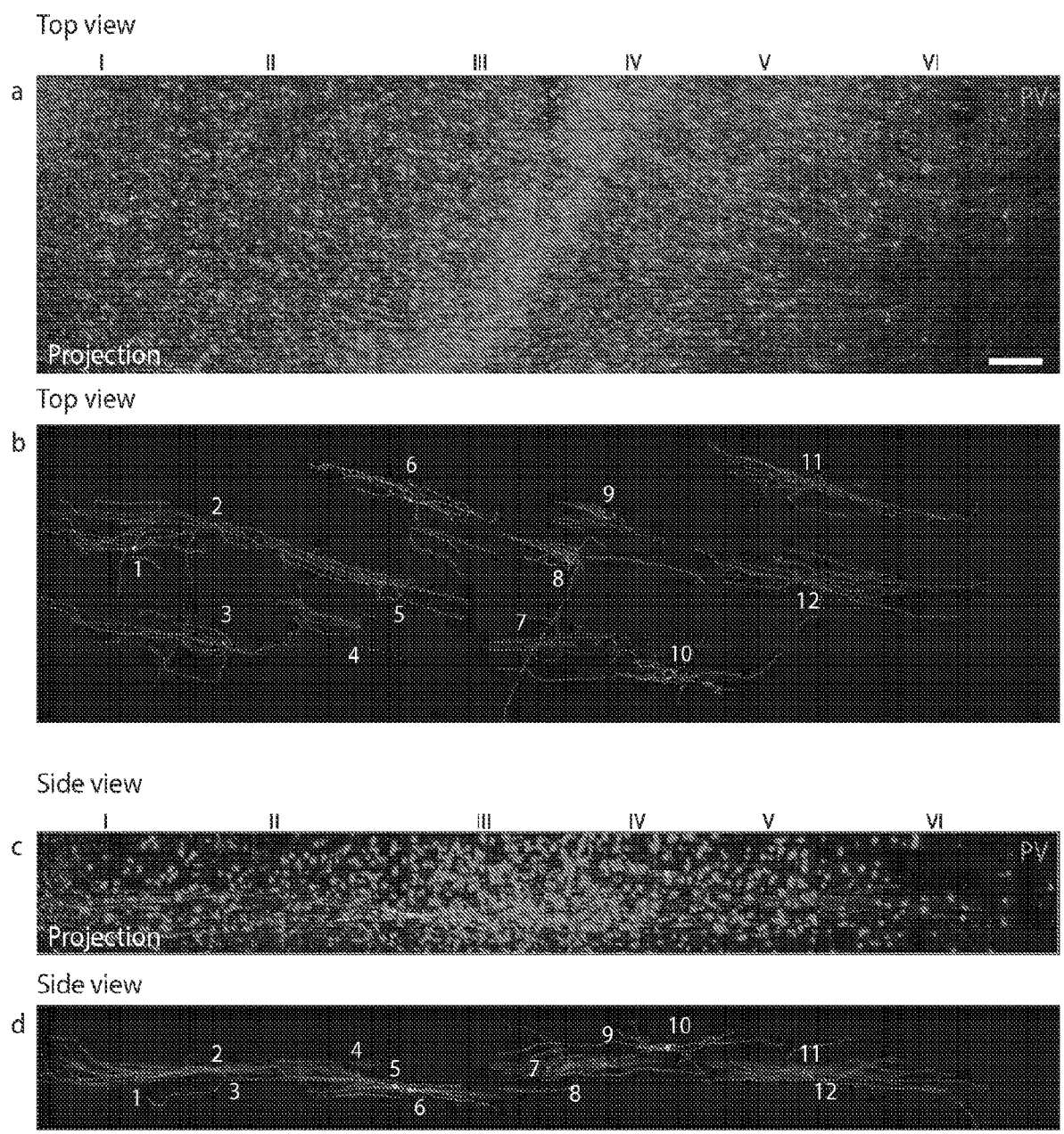
FIG. 19 is a collection of images showing results from the traced PV-positive neurons in the neocortex of a brain tissue sample from a subject with autism.

Example 19: Tracing of PV-Positive Neurons in a Brain Sample from an Autistic Subject A brain sample from an autistic subject was processed using CLARITY and PV-positive neurons in the neocortex were traced. The results are shown in FIG. 19. A 500 μm-thick intact block of frontal lobe (BA 10) of postmortem human brain (autism case, #AN13961; age, 7 years; sex, male; PMI, 25; storage, 82 months in 10% formalin at room temperature) was ETC cleared for a day and immune-stained for parvalbumin (PV) for three days: primary (1 day)—wash (0.5 day)—secondary (1 day)—wash (0.5 day). The stained block was imaged using the 25× water immersion objective. Neurons were selected randomly, with the stipulation that the cell body be located in the middle 125 μm of the block, and traced in Imarls software. Panel a: top view showing cortical laminar structure and traced PV-positive neurons. PV, red; scale bar, 200 μm. Panel b: traced neurons only (top view) showing relative positions of the neurons (1-13) in the cortical lamina. Number of iso- or hetero-neuronal dendritic bridges for each neuron can be found in Table 1, below. Panel c: side view. Panel d: side view, traced neurons only.

TABLE 1

Raw quantification data for the fourteen PV-positive neurons in autistic brain tissue shown in FIG. 6, Panel f and FIG. 19.

| Neuron | Layer | # of heteroneuronal bridges | # of isoneuronal bridges |
|---|---|---|---|
| 1 | 1/2 | 1 | 0 |
| 2 | 1/2 | 0 | 0 |
| 3 | 1/2 | 0 | 0 |
| 4 | 3 | 3 | 0 |
| 5 | 3 | 0 | 0 |
| 6 | 3 | 0 | 0 |
| 7 | 4 | 2 | 0 |
| 8 | 4 | 6 | 1 |
| 9 | 4 | 3 | 4 |
| 10 | 5/6 | 14 | 0 |
| 11 | 5/6 | 4 | 4 |
| 12 | 5/6 | 4 | 2 |
| m* | 5/6 | 31 | 21 |
| n* | 5/6 | 4 | 9 |

Figure 20:
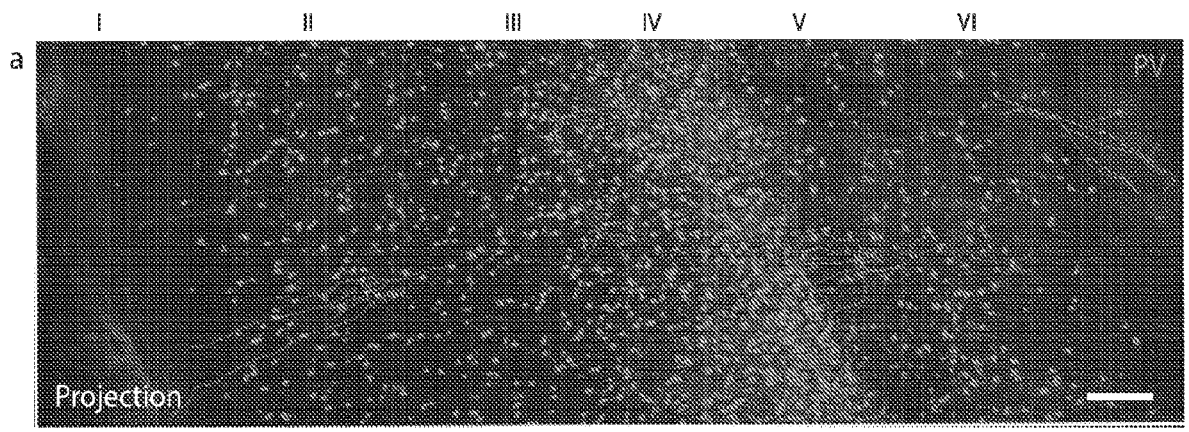
FIG. 20 is a collection of images showing results from the traced PV-positive neurons in the neocortex of a brain tissue sample from a normal control subject.
Figure 20:
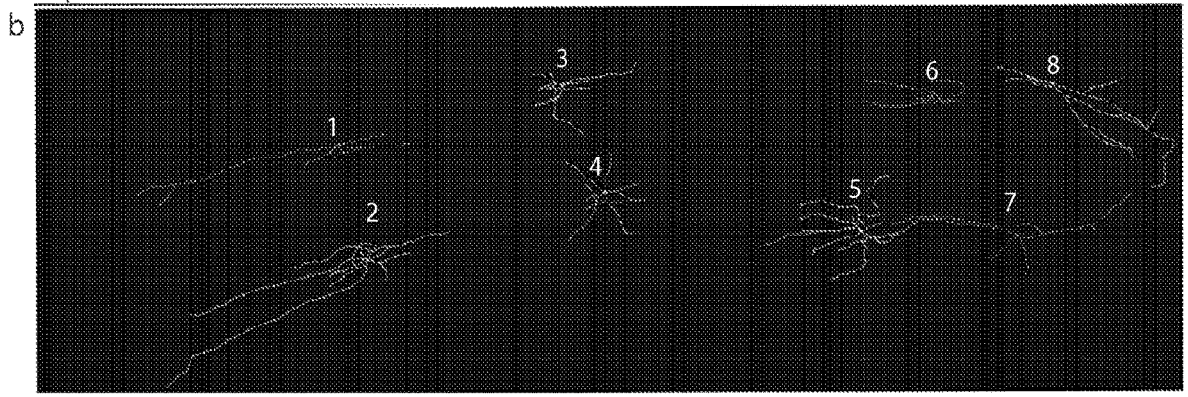
Figure 20:
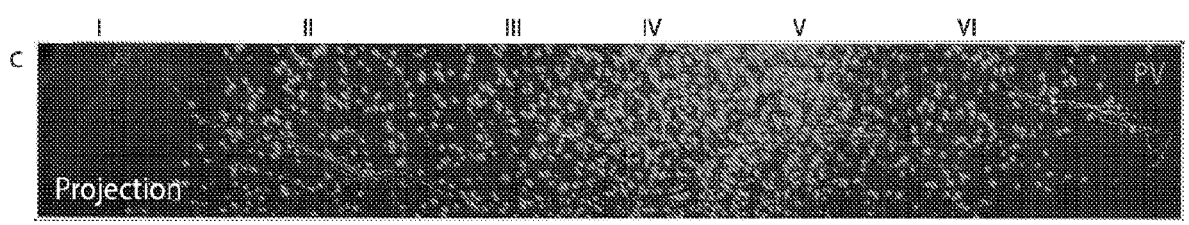
Figure 20:
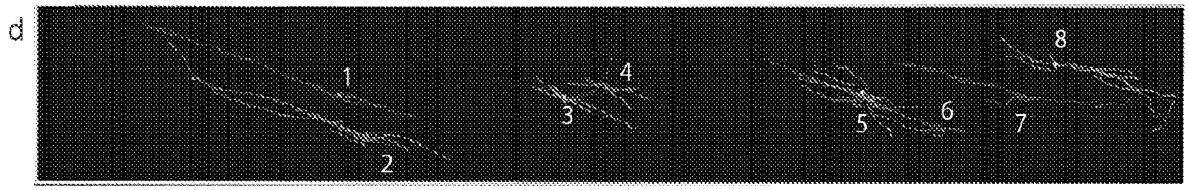

Example 20: Tracing of PV-Positive Neurons in a Brain Sample from a Normal Subject A brain sample from a normal subject was processed using CLARITY and PV-positive neurons in the neocortex were traced. The results are shown in FIG. 20. A 500 μm-thick intact block of frontal lobe (BA 10) of post-mortem human brain (normal control case for #AN13961 shown in FIG. 19, #AN10251; age, 10 years; sex, male; PMI, 19.83) was ETC cleared for a day and immune-stained for parvalbumin (PV) for three days: primary (1 day)—wash (0.5 day)—secondary (1 day)—wash (0.5 day). The stained block was imaged using the 25× water immersion objective. Neurons were selected randomly, with the stipulation that the cell body be located in the middle 125 μm of the block, and traced in Imarls software. Panel a: top view showing cortical laminar structure and traced PV-positive neurons. PV, red; scale bar, 200 μm. Panel b: the traced neurons only (top view) showing relative positions of neurons (1-8) in the cortical lamina. Number of iso- or hetero-neuronal dendritic bridges for each neuron can be found in Table 2, below. Panel c: side view. Panel d: side view, traced neurons only.

TABLE 2

Raw quantification data for the eight PV-positive neurons in normal control human brain tissue shown in FIG. 20

| Neuron | Layer | # of heteroneuronal bridges | # of isoneuronal bridges |
|---|---|---|---|
| 1 | 1/2 | 0 | 0 |
| 2 | 1/2 | 0 | 0 |
| 3 | 3 | 0 | 0 |
| 4 | 3 | 0 | 0 |
| 5 | 5/6 | 0 | 0 |
| 6 | 5/6 | 0 | 0 |
| 7 | 5/6 | 0 | 0 |
| 8 | 5/6 | 1 | 1 |

That which is claimed is:

1. A method of preparing a biological tissue specimen for microscopic analysis, the method comprising:
    fixing a biological tissue specimen obtained from a mammal by contacting the biological tissue specimen with a fixation agent and a plurality of hydrogel subunits, thereby cross-linking the hydrogel subunits to biomolecules within the biological tissue specimen to produce biomolecule-bound hydrogel subunits;
    polymerizing the biomolecule-bound hydrogel subunits to form a hydrogel-embedded biological tissue specimen; and
    electrophoresing the hydrogel-embedded biological tissue specimen to remove a plurality of cellular components from the specimen and form a cleared hydrogel-embedded biological tissue specimen.

2. The method according to claim 1, wherein the cellular components comprise lipids.

3. The method according to claim 1, wherein the hydrogel-embedded biological tissue specimen is electrophoresed using a buffer solution that comprises an ionic surfactant.

4. The method according to claim 3, wherein the ionic surfactant is sodium dodecyl sulfate.

5. The method according to claim 1, wherein the hydrogel-embedded biological tissue specimen is electrophoresed using a voltage ranging from about 10 to about 60 volts.

6. The method according to claim 1, wherein the hydrogel-embedded biological tissue specimen is electrophoresed for a period of time ranging from about 15 minutes up to about 10 days.

7. The method according to claim 1, further comprising incubating the cleared biological tissue specimen in a mounting medium that has a refractive index that matches that of the cleared biological tissue specimen.

8. The method according to claim 7, wherein the mounting medium increases the optical clarity of the cleared biological tissue specimen.

9. The method according to claim 7, wherein the mounting medium comprises glycerol.

10. The method according to claim 1, wherein the microscopic analysis is selected from the group consisting of optical microscopy, laser microscopy, electron microscopy, and scanning probe microscopy.

11. The method according to claim 1, wherein fixing the biological tissue specimen comprises contacting the hydrogel-embedded biological tissue specimen with a paraformaldehyde.

12. The method according to claim 1, wherein the hydrogel subunits comprise an acrylamide.

13. The method according to claim 1, wherein polymerizing the hydrogel subunits comprises thermal crosslinking.

14. The method according to claim 1, wherein the method further comprises contacting the biological tissue specimen with a polypeptide, nucleic acid, or small molecule.

15. The method according to claim 14, wherein the contacting comprises electrophoresis, hydrodynamic pressure, ultrasonic vibration, solute contrasts, microwave radiation, or vascular circulation.

16. The method according to claim 14, wherein the polypeptide, nucleic acid, or small molecule comprises a component that can be rendered visible when the biological tissue specimen is microscopically analyzed.

17. The method according to claim 1, wherein the biological tissue is central nervous system (CNS) tissue.

18. The method according to claim 17, wherein the CNS tissue is a whole brain.

19. The method of claim 1, further comprising:
imaging the cleared biological tissue specimen with a microscope.

20. The method according to claim 19, wherein the microscope is an optical microscope, laser microscope, electron microscope, or a scanning probe microscope.

21. The method according to claim 1, further comprising labelling cellular or subcellular aspects of the biological tissue specimen by transporting one or more small molecules, nucleic acids or proteins into the biological tissue specimen.

22. The method according to claim 21, further comprising removing one or more of the small molecules, nucleic acids, or proteins that were previously transported into the biological tissue specimen.

23. A method of preserving a biological tissue specimen, the method comprising:
fixing a biological tissue specimen obtained from a mammal by contacting the biological tissue specimen with a fixation agent and a plurality of hydrogel subunits, thereby cross-linking the hydrogel subunits to biomolecules within the biological tissue specimen to produce biomolecule-bound hydrogel subunits;
polymerizing the biomolecule-bound hydrogel subunits to form a hydrogel-embedded biological tissue specimen; and
electrophoresing the hydrogel-embedded biological tissue specimen to remove a plurality of cellular components from the specimen and form a cleared biological tissue specimen.

24. The method according to claim 23, further comprising storing the cleared biological tissue specimen in a mounting medium.

25. The method according to claim 23, further comprising analyzing the cleared biological tissue specimen for evaluation, diagnosis, or prognosis of a pathological state.

26. The method according to claim 23, wherein the biological tissue specimen is a biopsy specimen or an autopsy specimen.

27. The method according to claim 25, wherein the pathological state is cancer, immune system dysfunction, neuropsychiatric disease, endocrine/reproductive disease, cardiovascular/pulmonary disease, musculoskeletal disease, or gastrointestinal disease.

28. The method according to claim 23, wherein the biological tissue specimen comprises normal tissue, and wherein the method further comprises analyzing the biological tissue specimen to evaluate cell, tissue, organ or system function and/or relationships between cells and tissues, including during development.

29. The method according to claim 23, further comprising conducting a genetic, transcriptomic, genomic, proteomic, metabolomic and/or drug screening analysis on the biological tissue specimen.

30. The method according to claim 23, further comprising storing the cleared biological tissue specimen for future analysis, assessment, or functionalization.

31. The method according to claim 23, wherein the hydrogel-embedded biological tissue specimen is electrophoresed using a buffer solution that comprises an ionic surfactant.

32. The method according to claim 1, wherein the biomolecules within the biological tissue specimen comprise cells, proteins, or nucleic acids.

33. The method according to claim 23, wherein the biomolecules within the biological tissue specimen comprise cells, proteins, or nucleic acids.

* * * * *